(12) United States Patent
Lutz et al.

(10) Patent No.: US 10,537,545 B2
(45) Date of Patent: Jan. 21, 2020

(54) CERAMIDE DERIVATIVES AS ANTICANCER AGENTS

(71) Applicant: Rutgers, The State University of New Jersey, New Brunswick, NJ (US)

(72) Inventors: Richard Lutz, New Brunswick, NJ (US); Eric Andrianasolo, New Brunswick, NJ (US); Paul Falkowski, New Brunswick, NJ (US); Eileen White, New Brunswick, NJ (US); Liti Haramaty, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/746,368

(22) PCT Filed: Jul. 19, 2016

(86) PCT No.: PCT/US2016/042997
§ 371 (c)(1),
(2) Date: Jan. 19, 2018

(87) PCT Pub. No.: WO2017/015301
PCT Pub. Date: Jan. 26, 2017

(65) Prior Publication Data
US 2018/0207123 A1    Jul. 26, 2018

Related U.S. Application Data

(60) Provisional application No. 62/194,655, filed on Jul. 20, 2015.

(51) Int. Cl.
| | | |
|---|---|---|
| *C07C 233/18* | (2006.01) | |
| *A61K 31/232* | (2006.01) | |
| *A61K 45/06* | (2006.01) | |
| *A61K 31/164* | (2006.01) | |
| *A61K 31/352* | (2006.01) | |
| *A61P 31/00* | (2006.01) | |
| *A61P 35/00* | (2006.01) | |
| *A61K 31/22* | (2006.01) | |
| *A61K 31/336* | (2006.01) | |

(52) U.S. Cl.
CPC .......... *A61K 31/232* (2013.01); *A61K 31/164* (2013.01); *A61K 31/22* (2013.01); *A61K 31/336* (2013.01); *A61K 31/352* (2013.01); *A61K 45/06* (2013.01); *A61P 31/00* (2018.01); *A61P 35/00* (2018.01); *C07C 233/18* (2013.01)

(58) Field of Classification Search
CPC .... C07C 233/18; C07C 235/02; C07C 233/49
See application file for complete search history.

(56) References Cited

U.S. PATENT DOCUMENTS

| | | | | |
|---|---|---|---|---|
| 5,103,002 | A | * | 4/1992 | Wieland ............. C07D 295/125 544/168 |
| 5,476,671 | A | * | 12/1995 | Cho ........................ A61K 8/68 424/401 |
| 6,664,288 | B1 | | 12/2003 | Pardee et al. |
| 7,838,645 | B2 | | 11/2010 | Baehrecke et al. |
| 8,183,395 | B2 | | 5/2012 | Falkowski et al. |
| 2010/0113585 | A1 | * | 5/2010 | Falkowski ............ C07C 69/007 514/456 |
| 2011/0183915 | A1 | | 7/2011 | Pincus et al. |

FOREIGN PATENT DOCUMENTS

| | | | | |
|---|---|---|---|---|
| WO | 2000059517 | A1 | 10/2000 | |
| WO | WO-0059517 | A1 * | 10/2000 | ............. A61K 31/70 |
| WO | 2001072701 | A1 | 10/2001 | |
| WO | 2008109717 | A1 | 9/2008 | |
| WO | WO-2008109717 | A1 * | 9/2008 | ........... C07C 69/007 |

OTHER PUBLICATIONS

R. Lutz, Marine Natural Product Discovery in Extreme Environments (2017).*
E. Andrianasolo et al., 74 Journal of Natural Products, 842-846 (2011).*
E. Andrianasolo et al., Deep-Sea Hydrothermal Vents as a New Source of Drug Discovery in 36 Studies in Natural Products Chemistry (2012).*
A.S. Alban et al., 24 Journal of Enzyme Inhibition and Medicinal Chemistry, 844-849 (2009) (Year: 2009).*
Basmadjian et al., 2 Frontiers in Chemistry (2014) (Year: 2014).*
G. M. Cragg et al., 109 Chemical Reviews, 3012-3043 (2009) (Year: 2009).*
Andrianasolo, et al., "Ammonificins A and B, Hydroxyethylamine Chroman Derivatives from a Cultured Marine Hydrothermal Vent Bacterium, Thermovibrio ammonificans", J Nat Prod 72(6), 1216-1219 (2009).
Andrianasolo, et al., "Ammonificins C and D, Hydroxyethylamine Chromene Derivatives from a Cultured Marine Hydrothermal Vent Bacterium, Thermovibrio ammonificans", Mar Drugs 10(10), 200-2311 (2012).

(Continued)

*Primary Examiner* — Alexander R Pagano
(74) *Attorney, Agent, or Firm* — Viksnins Harris Padys Malen LLP

(57) ABSTRACT

The invention provides a compound of formula (I): (I) wherein $R^1$-$R^4$ have any of the values defined in the specification, as well as compositions comprising a compound of formula (I) and methods for treating diseases (e.g. cancer).

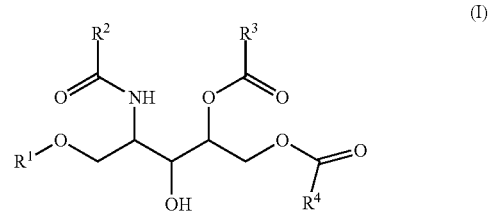

20 Claims, 16 Drawing Sheets

(56) References Cited

OTHER PUBLICATIONS

Andrianasolo, et al., "Apoptosis-Inducing Galactolipids from a Cultured Marine Diatom, Phaeodactylum tricornutum", J Nat Prod 71(7), 1197-1201 (2008).

Andrianasolo, "Bathymodiolamides A and B, Ceramide Derivatives from a Deep-Sea Hydrothermal Vent Invertebrate Mussel, *Bathymodiolus thermophilus*", J. Nat. Prod. 74(4), 842-846 (2011).

Andrianasolo, et al., "Induction of Apoptosis by Diterpenes from the Soft Coral *Xenia elongata*", J Nat Prod 70(10), 1551-1557 (2007).

Andrianasolo, et al., "Mode of Action of Diterpene and Characterization of Related Metabolites from the Soft Coral, *Xenia elongata*", Mar Drugs 12(2), 1102-1115 (2014).

Barth, et al., "Ceramide-based therapeutics for the treatment of cancer", Anticancer Agents Med Chem 11(9), 911-919 (2011).

Cuervo, "Autophagy: many paths to the same end", Mol Cell Biochem 263(1-2), 55-72 (2004).

Fulda, "Tumor resistance to apoptosis", Int J Cancer 124(3), 511-515 (2009).

Lauber, et al., "Clearance of apoptotic cells: getting rid of the corpses", Mol Cell 14(3), 277-287 (2004).

Okada, et al., "Pathways of apoptotic and non-apoptotic death in tumour cells", Nat Rev Cancer 4(8), 592-603 (2004).

Patent Cooperation Treaty, International Searching Authority, Search Report and Written Opinion for PCT/US2016/042997, 12 pages, dated Oct. 19, 2016.

Ramos, et al., "Prevalence of necrosis in C2-ceramide-induced cytotoxicity in NB16 neuroblastoma cells", Mol Pharmacol 64(2), 502-511 (2003).

Ricci, et al., "Chemotherapeutic approaches for targeting cell death pathways", Oncologist 11(4), 342-357 (2006).

Rodriguez-Enriquez, et al., "Role of mitochondrial permeability transition pores in mitochondrial autophagy", Int J Biochem Cell Biol 36(12), 2463-2472 (2004).

Vandenabeele, et al., "Molecular mechanisms of necroptosis: an ordered cellular explosion", Nat Rev Mol Cell Biol 11(10), 700-714 (2010).

Wani, et al., "Plant antitumor agents. VI. The isolation and structure of taxol, a novel antileukemic and antitumor agent from Taxus brevifolia", J Am Chem Soc 93(9), 2325-2327 (1971).

* cited by examiner

CERAMIDE DERIVATIVES AS ANTICANCER AGENTS

PRIORITY

This application claims priority to U.S. Provisional Application No. 62/194,655, filed 20 Jul. 2015. The entire content of this United States Provisional Application is incorporated herein by reference.

GOVERNMENT FUNDING

This invention was made with government support under R37 CA53370 awarded by the National Institutes of Health. The government has certain rights in the invention.

BACKGROUND

Certain compounds that contain lipid can induce apoptosis and act as tumor-suppressors, because a variety of stress stimuli cause apoptosis by increasing intracellular ceramide to initiate apoptotic signaling. Most current anticancer drugs kill actively dividing cells by the induction of apoptosis (Fulda S, Int J Cancer, 2009, 124, 11-515). In addition to this "classical" cancer chemotherapy, approaches that block molecular pathways involved in tumor cell proliferation and therapies that induce alternative cell death pathways are of interest for drug development (Ricci M S and Zong W X, Oncologist, 2006, 11, 42-357). Apoptotic cell death involves a series of events leading to characteristic changes in cell morphology, including loss of cell membrane asymmetry, nuclear fragmentation, chromatin condensation, chromosomal DNA fragmentation and activation of caspases. Unfortunately, cancer cells often acquire resistance to agents that activate the apoptotic pathway. Therefore, alternative cell death pathways are being examined for exploitation in cancer chemotherapy.

Programmed cell death has been classified based on morphological criteria into several categories (Okada H, Mak T W, Nat Rev Cancer, 2004, 4, 592-603). The most extensively studied is apoptosis, or type I cell death, which is characterized by cell rounding, membrane blebbing, cytoplasmic condensation and fragmentation, nuclear pyknosis, and chromatin condensation/fragmentation. Apoptotic bodies are rapidly phagocytized and digested by macrophages or neighboring cells (Lauber K, et al., Mol Cell, 2004, 14, 277-87). The second type of programmed cell death is autophagy which is rarely investigated, or type II cell death, which is characterized by the appearance of abundant autophagic vacuoles in the cytoplasm, and enlargement of the endoplasmic reticulum and the Golgi apparatus (Cuervo A M. Mol Cell Biochem, 2004, 263, 55-72; and Meijer A J, et al., Int J Biochem Cell Biol, 2004, 36, 2463-72).

The type III cell death is necrosis, which was before regarded as an unregulated and uncontrollable process. Evidence now reveals that necrosis can also occur in a regulated manner. The initiation of programmed necrosis, 'necroptosis', by death receptors (such as tumour necrosis factor receptor 1) requires the kinase activity of receptor-interacting protein 1 (RIP1; also known as RIPK1) and RIP3 (also known as RIPK3), and its execution involves the active disintegration of mitochondrial, lysosomal and plasma membranes. Necroptosis participates in the pathogenesis of diseases, including ischaemic injury, neurodegeneration and viral infection, thereby representing an attractive target for the avoidance of unwarranted cell death (Vandenabeele P., et al., Nature Reviews Molecular Cell Biology, 2010, 11, 700-714).

There are a number of cytotoxic agents that are currently being used or studied for the treatment of cancer. One of these, Paclitaxel, (also referred to as TAXOL®) was first identified in 1971 by Wani and collaborators (Wani M C et al. J. Am. Chem, Soc., 1971, 93, 2325-2327) following a screening program of plant extracts of National Cancer Institute. This complex diterpene shows cytotoxic activity against several types of tumors and is presently used in the treatment of some cancers such as ovarian and breast cancers. Clinical studies suggest that TAXOL® could eventually be used in the treatment of over 70% of human cancers.

Paclitaxel differs from other cytotoxic drugs by its unique mechanism of action. It interferes with cell division by manipulating the molecular regulation of the cell cycle. Paclitaxel binds to tubulin, the major structural component of microtubules that are present in all eukaryotic cells. Unlike other antimitotic agents such as vinca alkaloids and colcichine, which inhibit the polymerization of tubulin, paclitaxel promotes this assembly of tubulin and stabilizes the resulting microtubules. This event leads to the interruption of cell division, and ultimately to cell death. The antitumor property of taxoid compounds has also lead to the generation of new anticancer drugs derived from taxanes. Taxortere™ (sold by Rhone-Poulenc Rorer), which is produced from 10-deacetylbaccatin III hemysynthesis, is currently used in the treatment of ovarian and breast cancers. While agents such as TAXOL® and Taxotere have made an advance in the treatment of metastatic ovarian and metastatic breast cancer, the majority of those treated still ultimately succumb to these diseases. No single drug or drug combination is curative for advanced metastatic cancer and patients typically succumb to the cancers in several years. Thus, new drugs or combinations that can prolong onset of life-threatening tumors and/or improve quality of life by further reducing tumor-load are very important. (see U.S. Pat. No. 6,664,288)

Several groups have observed necrosis-like cell death that appears to occur in a caspase independent manner. Furthermore, nonapoptotic cell death appears to provide a compensatory mechanism for cell killing when apoptotic regulators such as caspases and Apaf1 are compromised. Thus, it would be beneficial to determine methods, enzymatic pathways and compounds that induce such nonapoptotic mechanisms to compensate when programmed death by apoptosis is compromised. (see U.S. Pat. No. 7,838,645)

Another interesting discovery was on the ability of small molecules that can cause necrosis in cancer cells but do not affect normal cells. These small molecules like Nutlin-2 can bind to HDM-2 in combination with a membrane resident component like Guanidinylated biphenyl. This formulation can treat cancer by targeting deficient p53 or non-p53 cancer cells and causing membranolysis in a subject having a plurality of cancer cells. (see United States Patent Application Publication Number US2011/0183915A1).

Recently, small molecule diterpenes belonging to xenicane skeleton have been discovered. These molecules induce apoptosis upstream of Bax and Bak in tumor cells. The diterpene affects cell in a manner similar to that of HSP90 and HDAC inhibitors and in a manner opposite of PI3 kinase/mTOR inhibitors. The diterpene also inhibits selectively HDAC6 and represents a new model structure of selective HDAC inhibitors which will contribute to the development of HDAC practical isoform selective. The vast majority of human solid tumors are of epithelial origin, and defects in apoptosis, mostly upstream of Bax and Bak, play important roles in both tumor suppression and mediation of chemotherapeutic response. (see U.S. Pat. No. 8,183,395).

Andrianasolo, E H, et al., *Nat. Prod.*, 2011, 74 (4), 842-846 reported the isolation of two ceramide derivatives, bathymodiolamides A (1) and B (2), from the deep-sea hydrothermal vent invertebrate mussel *Bathymodiolus thermophilus*. The molecular structures of these compounds were determined using a combination of NMR spectroscopy, mass spectrometry, and chemical degradation. Biological activities were assessed in a ApopScreen cell-based screen for apoptosis induction and potential anticancer activity. The results showed that 1 and 2 inhibit the growth of two cancer cell lines [HeLa (cervical cancer) ($IC_{50}$ 0.4 µM for 1 and $IC_{50}$ 0.5 µM for 2) and MCF7 (breast cancer) ($IC_{50}$ 0.1 µM for 1 and $IC_{50}$ 0.2 µM for 2)].

Currently there is a need for compositions and methods that are useful for treating or preventing cancer.

SUMMARY

It has been determined that certain ceramide like compounds that induce necrosis can complement the effect of compounds that induce apoptosis in the treatment of cancer.

Accordingly in one embodiment the invention provides a compound of formula I:

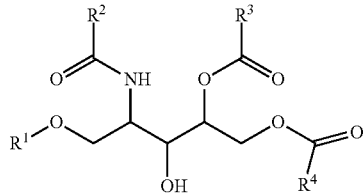

or a salt thereof, wherein:
$R^1$ is $R^a$—$(OCH_2CH_2)_n$—;
$R^2$ is ($C_4$-$C_{25}$)alkyl or ($C_4$-$C_{25}$)alkenyl;
$R^3$ is ($C_4$-$C_{25}$)alkyl or ($C_4$-$C_{25}$)alkenyl;
$R^4$ is ($C_4$-$C_{25}$)alkyl or ($C_4$-$C_{25}$)alkenyl;
$R^a$ is ($C_1$-$C_6$)alkyl; and
n is 0, 1, 2, 3, 4, 5, 6, 7, 8, 9, or 10.

In another embodiment the invention provides a composition comprising 1) an apoptosis inducing compound, and 2) a compound of formula I:

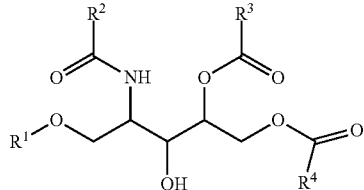

or a pharmaceutically acceptable salt thereof, wherein:
$R^1$ is H or $R^a$—$(OCH_2CH_2)_n$—;
$R^2$ is ($C_4$-$C_{25}$)alkyl or ($C_4$-$C_{25}$)alkenyl;
$R^3$ is ($C_4$-$C_{25}$)alkyl or ($C_4$-$C_{25}$)alkenyl;
$R^4$ is ($C_4$-$C_{25}$)alkyl or ($C_4$-$C_{25}$)alkenyl;
$R^a$ is ($C_1$-$C_6$)alkyl; and
n is 0, 1, 2, 3, 4, 5, 6, 7, 8, 9, or 10.

In another embodiment the invention provides a method for treating cancer in an animal comprising administering to the animal: 1) an apoptosis inducing compound, and 2) a compound of formula I:

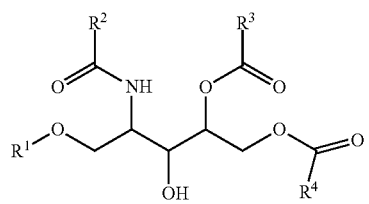

or a pharmaceutically acceptable salt thereof, wherein:
$R^1$ is H or $R^a$—$(OCH_2CH_2)_n$—;
$R^2$ is ($C_4$-$C_{25}$)alkyl or ($C_4$-$C_{25}$)alkenyl;
$R^3$ is ($C_4$-$C_{25}$)alkyl or ($C_4$-$C_{25}$)alkenyl;
$R^4$ is ($C_4$-$C_{25}$)alkyl or ($C_4$-$C_{25}$)alkenyl;
$R^a$ is ($C_1$-$C_6$)alkyl; and
n is 0, 1, 2, 3, 4, 5, 6, 7, 8, 9, or 10.

In another embodiment the invention provides a method for treating cancer in an animal comprising administering to the animal a compound of formula (I):

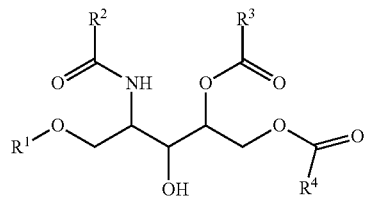

or a pharmaceutically acceptable salt thereof, wherein:
$R^1$ is H or $R^a$—$(OCH_2CH_2)_n$—;
$R^2$ is ($C_4$-$C_{25}$)alkyl or ($C_4$-$C_{25}$)alkenyl;
$R^3$ is ($C_4$-$C_{25}$)alkyl or ($C_4$-$C_{25}$)alkenyl;
$R^4$ is ($C_4$-$C_{25}$)alkyl or ($C_4$-$C_{25}$)alkenyl;
$R^a$ is ($C_1$-$C_6$)alkyl; and
n is 0, 1, 2, 3, 4, 5, 6, 7, 8, 9, or 10.

In another embodiment the invention provides a pharmaceutical composition comprising, 1) a pharmaceutically acceptable diluent or carrier and 2) a compound of formula (I):

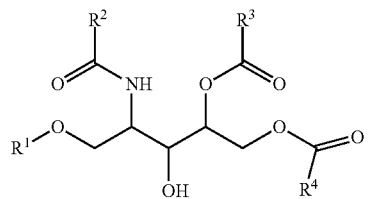

or a pharmaceutically acceptable salt thereof, wherein:
$R^1$ is H or $R^a$—$(OCH_2CH_2)_n$—;
$R^2$ is ($C_4$-$C_{25}$)alkyl or ($C_4$-$C_{25}$)alkenyl;
$R^3$ is ($C_4$-$C_{25}$)alkyl or ($C_4$-$C_{25}$)alkenyl;
$R^4$ is ($C_4$-$C_{25}$)alkyl or ($C_4$-$C_{25}$)alkenyl;
$R^a$ is ($C_1$-$C_6$)alkyl; and
n is 0, 1, 2, 3, 4, 5, 6, 7, 8, 9, or 10.

In another embodiment the invention provides a compound of formula (I) or a pharmaceutically acceptable salt thereof for use in medical therapy.

In another embodiment the invention provides a compound of formula (I):

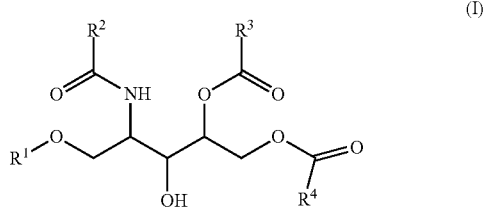

(I)

or a pharmaceutically acceptable salt thereof, wherein:
$R^1$ is H or $R^a$—$(OCH_2CH_2)_n$—;
$R^2$ is ($C_4$-$C_{25}$)alkyl or ($C_4$-$C_{25}$)alkenyl;
$R^3$ is ($C_4$-$C_{25}$)alkyl or ($C_4$-$C_{25}$)alkenyl;
$R^4$ is ($C_4$-$C_{25}$)alkyl or ($C_4$-$C_{25}$)alkenyl;
$R^a$ is ($C_1$-$C_6$)alkyl; and
n is 0, 1, 2, 3, 4, 5, 6, 7, 8, 9, or 10;
for the prophylactic or therapeutic treatment of cancer in combination with an apoptosis inducing compound.

In another embodiment the invention provides the use of compound of formula (I):

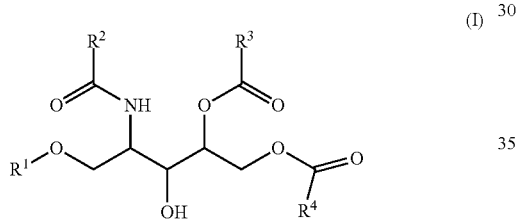

(I)

or a pharmaceutically acceptable salt thereof, wherein:
$R^1$ is H or $R^a$—$(OCH_2CH_2)_n$—;
$R^2$ is ($C_4$-$C_{25}$)alkyl or ($C_4$-$C_{25}$)alkenyl;
$R^3$ is ($C_4$-$C_{25}$)alkyl or ($C_4$-$C_{25}$)alkenyl;
$R^4$ is ($C_4$-$C_{25}$)alkyl or ($C_4$-$C_{25}$)alkenyl;
$R^a$ is ($C_1$-$C_6$)alkyl; and
n is 0, 1, 2, 3, 4, 5, 6, 7, 8, 9, or 10;
to prepare a medicament for treating cancer in an animal (e.g. a mammal such as a human), in combination with an apoptosis inducing compound.

In another embodiment the invention provides a kit comprising packaging material and a compound of formula (I) or a salt thereof.

In another embodiment the invention provides a kit comprising packaging material and a pharmaceutical composition of the invention.

The invention also provides processes and intermediates disclosed herein that are useful for preparing or isolating a compound of formula (I) or a salt thereof.

This invention relates to the ability of various bathymodiolamides, from the deep-sea hydrothermal vent invertebrate mussel, *Bathymodiolus thermophilus* to induce necrosis in tumor cells. The molecular structures of these compounds were determined using a combination of NMR, mass spectrometry and chemical degradation. Biological activities were assessed in an ApopScreen cell-based screen for apoptosis-induction and couple with cytotoxicity assay as well as LDH assay.

Bathymodiolamides, did not induce apoptosis when tested with the ApopScreen assay using W2 (apoptosis competent) and D3 (apoptosis defective, Bax and Bak null cells, capable of necrosis), these compounds kill D3 cells and inhibit the growth of several cancer lines in a cytotoxic assay; consequently these compounds kill cancer cells via nonapoptotic pathway. Lactate Dehydrogenase (LDH) assay revealed that these compounds induce necrosis.

Necroptosis is a recently discovered programmed necrosis. Evidence demonstrated the importance of necroptosis in cell death. Necrostatin is a specific inhibitor of necroptosis. Necrostatin inhibits receptor-interacting protein 1 (RIP1) kinase and programmed necrosis. Bathymodiolamides show an opposite effect of necrostatin when co-administered to D3 cells (apoptosis defective, bax and bak null cells). Since bathymodiolamides induce necrosis they can be used as anticancer agents acting alone or in combination of other anticancer agents and preferably with apoptosis inducers in the family of diterpene compounds having xenican skeleton.

This present invention includes a method of inducing tumor cell necroptosis by administering to a patient in need thereof an amount of a bathymodiolamide effective to induce tumor cell necroptosis. Another aspect of the invention is a method of killing tumor cells by combination of apoptosis inducer agents and necroptosis inducer agents. Specific apoptosis inducers include diterpene compounds that can induce apoptosis upstream of Bax and Bak in the apoptosis pathways. In one embodiment the tumor cells are breast tumor cells.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

"Patient" means a mammal including a human.

"Effective amount" means an amount of any Bathymodiolamides or combination of any Bathymodioalmides and any diterpene compounds I-VI effective for producing a desired therapeutic effect.

Figure 13:
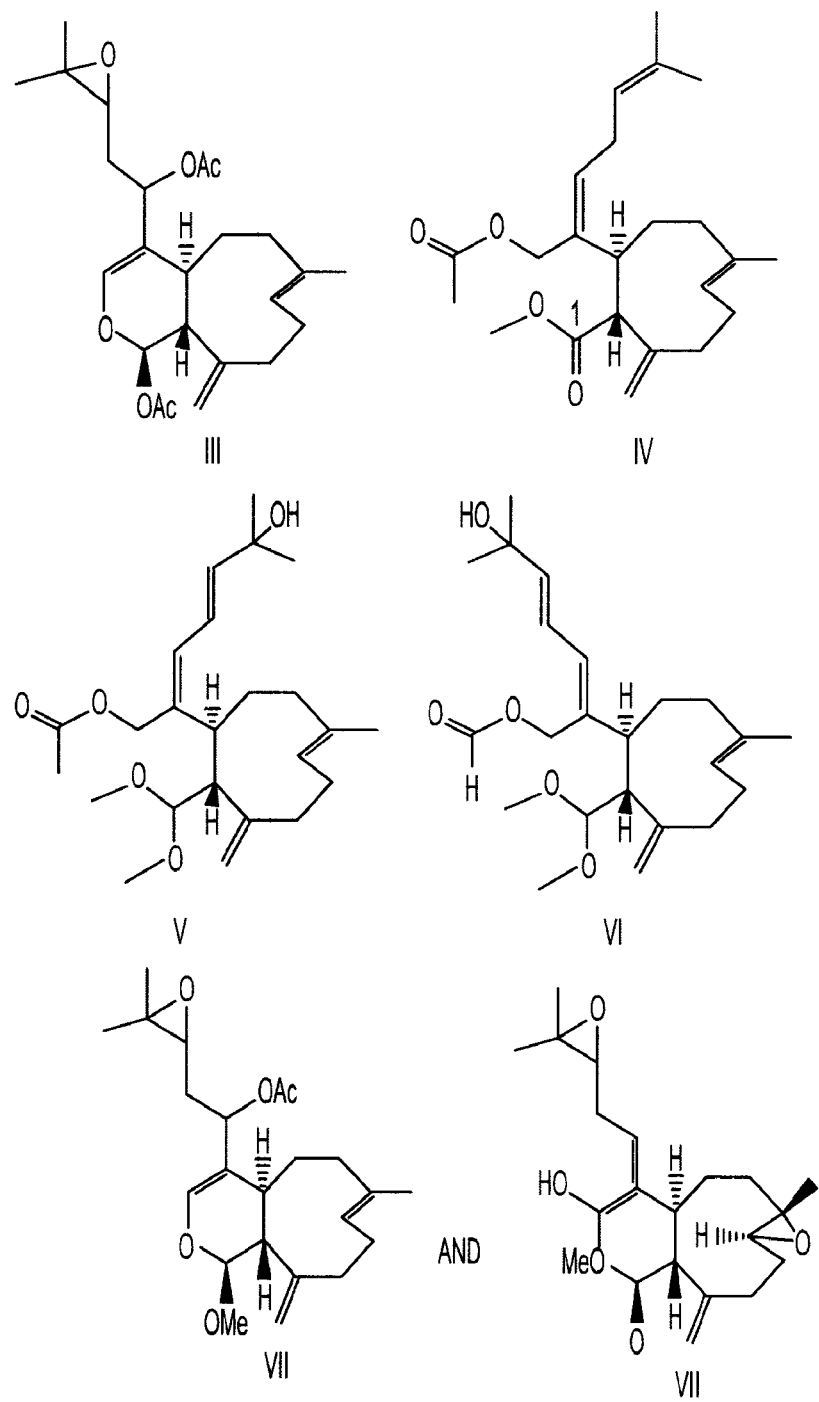
FIG. 13 shows diterpene compounds III-VIII that are apoptosis inducers.

"Treat" or "treatment" or "treating" mean to lessen, eliminate, inhibit, improve, alter, or prevent a disease, condition, or disorder, for example by administration of any Bathymodiolamides or co-administration of any Bathymodioalmides and any diterpene compounds I-VI (FIG. 13).

"Isolated" or "Purified" means a compound that exists apart from its native environment. "Isolated" or "Purified" includes compounds that are substantially free of biological material. In one embodiment, the invention provides a compound of formula (I) or a salt thereof that is isolated and purified.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents A specific value for n is 1, 2, 3, 4, 5, 6, 7, 8, 9, or 10.
A specific value for $R^2$ is $(C_9-C_{25})$alkyl.
A specific value for $R^2$ is $(C_9-C_{25})$alkenyl.
A specific value for $R^3$ is $(C_9-C_{25})$alkyl.
A specific value for $R^3$ is $(C_9-C_{25})$alkenyl.
A specific value for $R^4$ is $(C_9-C_{25})$alkyl.
A specific value for $R^4$ is $(C_9-C_{25})$alkenyl.
A specific value for $R^2$ is $(C_{11}-C_{20})$alkyl.
A specific value for $R^2$ is $(C_{11}-C_{20})$alkenyl.
A specific value for $R^3$ is $(C_{11}-C_{20})$alkyl.
A specific value for $R^3$ is $(C_{11}-C_{20})$alkenyl.
A specific value for $R^4$ is $(C_{11}-C_{20})$alkyl.
A specific value for $R^4$ is $(C_{11}-C_{20})$alkenyl.
A specific value for $R^a$ is methyl, ethyl, propyl, or isopropyl.
A specific value for $R^a$ is methyl.
A specific value for n is 0.

In one embodiment the invention provides a kit comprising packaging material and a compound of formula (I) or a salt thereof. In one embodiment the compound of formula (I) or the salt thereof is isolated. In one embodiment the kit further comprises instructions for administering the compound of formula (I) or the salt thereof to a mammal to treat cancer. In one embodiment the kit further comprises instructions for administering the compound of formula (I) or the salt thereof to a mammal in combination with another therapeutic agent to treat cancer. In one embodiment the therapeutic agent induces apoptosis in mammals. In one embodiment the packaging material is a flask, bottle, or vial.

In another embodiment the invention provides a kit comprising packaging material and a pharmaceutical composition of the invention. In one embodiment the kit further comprises instructions for administering the composition to a mammal to treat cancer. In one embodiment the kit further comprises instructions for administering the composition to a mammal in combination with another therapeutic agent to treat cancer. In one embodiment the therapeutic agent induces apoptosis in mammals. In one embodiment the packaging material is a flask, bottle, or vial.

In one embodiment the compound is not bathymodiolamide A or B.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In practice, a composition containing any Bathymodiolamides may be administered in any variety of suitable forms, for example, orally, by inhalation, topically, parenterally, or rectally. In one embodiment, the composition is administered orally, intramuscular, subcutaneous, intraocular, intrasynovial, colonical, peritoneal, transepithelial including transdermal, ophthalmic, sublingual, buccal, dermal, ocular, nasal inhalation via insufflations or by aerosol. Also, a composition containing a combination of any Bathymodiolamides and any diterpene compound may be administered in any variety of suitable forms cited above.

A composition containing any Bathymodiolamides or combination of any Bathymodiolamides and any diterpene compound may be presented in forms permitting administration by the most suitable route. The invention also relates to administering any Bathiodiolamides or combination of any Bathymodiolamides and any diterpene compound which is suitable for use as a medicament in a patient. These compositions may be prepared according to the customary methods, using one or more pharmaceutically acceptable adjuvants or excipients. The adjuvants comprise, inter alia, diluents, sterile aqueous media and various non-toxic organic solvent. The compositions may be presented in the form of oral dosage forms, or injectable solutions, or suspensions. Specific dosage forms include tablets, capsules, oily suspensions, aqueous suspensions, lozenges, troches, powders, granules, emulsions, syrups, and elixirs.

The choice of vehicle is generally determined in accordance with the solubility and chemical properties of the product, the particular mode of administration and provisions to be observed in pharmaceutical practice. When aqueous suspension are used they may contain emulsifying agents or agents which facilitate suspension. Diluents such as sucrose ethanol, polyols such as polyethylene glycol, propylene glycol and glycerol, and chloroform or mixtures thereof may also be used. In addition, any Bathymodiolamides or combination of any Bathymodiolamides and any diterpene may be incorporated into sustained-released preparations and formulations.

For parental administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutical acceptable salts, are used. The injectable forms must be fluid to the extent that it can be easily syringe, and proper fluidity can be maintained, for example, by the use of coating such as lecithin, by the maintenance of the required particle size in the case of dispersion and by the use of surfactants. Prolonged absorption of the injectable compositions can be brought about by use of agents delaying absorption, for example, aluminium monostearate and gelatin. The solutions of the salts of the products according to the invention are especially useful for administration by intramuscular or subcutaneous injection. Solutions of any Bathymodiolamides or combination of any Bathymodiolamides and any diterpenes compound I-VI as a free base or pharmacologically acceptable salt can be prepared in water suitably mixed with a surfactant such as hydroxypropyl-cellulose. Dispersions can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation microfiltration, and/or by various antibacterial and antifungal agents, for example, parabens, chlorobutanol, phenol, sorbic acid, thimerosal, and the like.

Sterile injectable solutions are prepared by incorporating any Bathymodiolamides or combination of Bathymodiolamides and any diterpene compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze drying technique, which yield a powder of the active ingredient plus any additional desired ingredient from previously sterile-filtered solution thereof.

Topical administration, gels (water or alcohol based), creams or ointments containing any of Bathymodiolamides or combination of any Bathymodiolamides and any diterpene compound may be used. Any Bathymodiolamides or combination of any Bathymodiolamides and diterpene compound may be also incorporated in a gel matrix base for application in a patch, which would allow a controlled release of compound through transdermal barrier.

For administration by inhalation, any Bathymodiolamides or combination of any Bathymodiolamides and diterpene compound may be dissolved or suspended in a suitable carrier for use in a nebulizer or a suspension or solution aerosol, or may be absorbed or adsorbed onto a suitable solid carrier for use in a dry powder inhaler.

The percentage of Bathymodiolamides or combination of Bathymodiolamides and diterpene compound in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 40, preferably about 0.001 to about 4, mg/kg body weight per day by inhalation, from about 0.01 to about 90, preferably 0.1 to 60, more specifically 0.5 to 8, mg/kg body weight per day by oral administration, and from about 0.001 to about 9, preferably 0.01 to 9. mg/kg body weight per day by intravenous administration. In each particular case, the doses are determined in accordance with the factors distinctive to the patient to be treated, such as age, weight, general state of health and other characteristic, which can influence the efficacy of the compound according to the invention.

Bathymodiolamides or combination of Bathymodiolamides and diterpene compound used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, any Bathymodiolamides or combination of any Bathymodiolamides and any diterpene compound may be administered 1 to 4 times per day. for other patients, it will be necessary to prescribe not more than one or two doses per day.

The invention will now be illustrated by the following non-limiting Examples.

EXAMPLES

The following general abbreviations may be used herein.
DMSO=Dimethyl Sulfoxide
DNA=Deoxyribonucleic acid
ESIMS=Electrospray Ionisation Mass Spectrometry
HPLC=High Pressure Liquid Chromatography
HRESIMS=High Resolution Electrospray Ionisation Mass Spectrometry
HRMALDITOFMS=High Resolution Matrix Assisted Laser Desorption Ionization Time Of Flight Mass Spectrometry
$IC_{50}$=The half maximal Inhibitory Concentration LRESIMS=Low Resolution Electrospray Ionisation Mass Spectrometry
MeOH=Methanol
MS=Mass Spectrometry
MS/MS=Tandem Mass Spectrometry Method
NMR=Nuclear Magnetic Resonance
RPHPLC=Reverse Phase High Pressure Liquid Chromatography
UV=Ultraviolet
IR=Infrared
FT-IR=Fourier Transform Infrared
LDH=Lactate Dehydrogenase
HDAC=Histone Deacetylase Example 1. Identification of Bathymodiolamides A-G General Experimental Procedures. Optical rotations were measured on a JASCO P 1010 polarimeter. UV and FT-IR spectra were obtained using Hewlett-Packard 8452A and Nicolet 510 instruments, respectively. All NMR spectra were recorded on a Bruker Avance DRX400 spectrometer, a Varian-400 instrument (400 MHz) and a Varian-500 instrument (500 MHz). Spectra were referenced to residual solvent resonances at $\delta_{H/C}$ 3.31/49.15 (CD$_3$OD). ESIMS data were acquired on a Waters Micromass LCT Classic mass spectrometer and a Varian 500-MS LC ion trap instrument. MALDITOFMS data were acquired on an ABI-MDS SCIEX 4800 instrument capable of performing true MS/MS for peptide analysis. HPLC separations were performed using Waters 510 HPLC pumps, a Waters 717 plus autosampler, and a Waters 996 photodiode array detector. All solvents were purchased as HPLC grade.

Animal Material. *Bathymodiolus thermophilus* was collected using the deep submergence vehicle DSV Alvin from an active hydrothermal vent along the Mid-Atlantic Ridge (Region: North, Location: Lucky Strike (LS), Dive Number: 3120, Date: Jul. 10, 1997, Latitude: 37° 17.63' N, Longitude: 32° 16.53' W, Depth: 1,733 m) and identified by Dr. R. C. Vrijenhoek (Department of Genetics, Rutgers, The State University of New Jersey) and DR. C. Vetriani (IMCS, Rutgers, The State University of New Jersey). A voucher specimen is available at the Center for Marine Biotechnology, IMCS, Rutgers The State University of New Jersey, New Brunswick, N.J. 08901 with collection number AD-MUS-LS-7/10/97.

Extraction and Isolation. *Bathymodiolus thermophilus* tissue (100 g wet mass) was extracted three times with MeOH to give a polar organic extract (850 mg). A portion of this extract (20 mg) was tested for induction of apoptosis and was found active. Therefore, the remaining organic extract was subjected to fractionation using solid-phase extraction on normal-phase silica to give four fractions, F1 to F4, eluted with hexanes, hexanes-EtOH, EtOH, and MeOH, in a series of increasingly hydrophilic solvent systems. The MeOH fraction (F4) had apoptosis induction activity. This fraction was further chromatographed by analytical RP HPLC (Phenomenex Luna C$_{18}$, 250×4.60 mm, isocratic elution 4:1 MeOH—H$_2$O, flow rate 1 mL/min) to yield 11.4 mg of 1 ($t_R$=11.5 min), 8.7 mg of 2 ($t_R$=9.5 min), 5.5 mg of 3 ($t_R$=8.5 min), 4 mg of 4 ($t_R$=12.5 min), 5 mg of 5 ($t_R$=10 min), 1 mg of 6 ($t_R$=12 min) and 1 mg of 7 ($t_R$=13 min).

Bathymodiolamide A (1): $[\alpha]^{24}_D$+10.8 (c 0.08, MeOH); IR $\nu_{max}$ (neat) 3350, 3250, 2900, 2850, 1640, 1450, 1050 cm$^{-1}$; $^1$H NMR and $^{13}$C NMR, (see Table 1 in *J. Nat. Prod.*, 2011, 74, 842-846.); HRMALDITOFMS m/z 804.6712 [M+H]$^+$ (calcd for C$_{49}$H$_{90}$NO$_7$, 804.6717).

Bathymodiolamide B (2): $[\alpha]^{24}_D$+10.9 (c 0.08, MeOH); IR $\nu_{max}$ (neat) 3350, 3250, 2900, 2850, 1640, 1450, 1050 cm$^{-1}$; $^1$H NMR and $^{13}$C NMR, (see Table 2 in *J. Nat. Prod.*, 2011, 74, 842-846.); HRMALDITOFMS m/z 730.5594 [M+Na]$^+$ (calcd for C$_{42}$H$_{77}$NNaO$_7$, 730.5598).

Bathymodiolamide C (3): $[\alpha]^{24}_D$+10.2 (c 0.08, MeOH); IR $\nu_{max}$ (neat) 3350, 3250, 2900, 2850, 1640, 1450, 1050 cm$^{-1}$; $^1$H NMR and $^{13}$C NMR, Table 2; HRMALDITOFMS nm/z 1054.8998 [M+H]$^+$ (calcd for C$_{66}$H$_{120}$NO$_8$, 1054.9008).

Bathymodiolamide D (4): $[\alpha]^{24}_D$+10.4 (c 0.08, MeOH); IR $\nu_{max}$ (neat) 3350, 3250, 2900, 2850, 1640, 1450, 1050 cm$^{-1}$; $^1$H NMR and $^{13}$C NMR, Table 3; HRMALDITOFMS m/z 780.6340 [M+H]$^+$ (calcd for C$_{46}$H$_{86}$NO$_8$, 780.6348).

Bathymodiolamide E (5): $[\alpha]^{24}_D$+10.1 (c 0.08, MeOH); IR $\nu_{max}$ (neat) 3350, 3250, 2900, 2850, 1640, 1450, 1050 cm$^{-1}$; $^1$H NMR and $^{13}$C NMR, Table 4; HRMALDITOFMS m/z 1080.8408 [M+Na]$^+$ (calcd for C$_{64}$H$_{115}$NNaO$_{10}$, 1080.8413).

Bathymodiolamide F (6): $[\alpha]^{24}_D$+10.5 (c 0.08, MeOH); IR $\nu_{max}$ (neat) 3350, 3250, 2900, 2850, 1640, 1450, 1050 cm$^{-1}$; HRMALDITOFMS m/z 740.6029 [M+H]$^+$ (calcd for C$_{43}$H$_{82}$NO$_8$, 740.6035).

Bathymodiolamide G (7): $[\alpha]^{24}_D$+10.6 (c 0.08, MeOH); IR $\nu_{max}$ (neat) 3350, 3250, 2900, 2850, 1640, 1450, 1050 cm$^{-1}$; HRMALDITOFMS m/z 828.6549 [M+H]$^+$ (calcd for C$_{47}$H$_{90}$NO$_{10}$, 828.6559).

TABLE 1

Results from Cytotoxic assay for Bathymodiolamide A (1)

| µg*0.01/ml | Growth HELA | CTRL HELA | Growth MCF7 | CTRL MCF7 |
|---|---|---|---|---|
| 360 | 0.31 | 0.56 | 0.11 | 0.15 |
| 72 | 0.43 | 0.78 | 0.29 | 0.42 |
| cntrl | 0.55 | 1 | 0.7 | 1 |

TABLE 2

Bathymodiolamide C(3) NMR data 600 MHz in CD3OD

| Position | $\delta_C$, mult. | $\delta_H$ (J in Hz) | HMBC$^a$ |
|---|---|---|---|
| 1-a 1-b | 63.3 CH2 | 4.00, d (4.4) 4.00, d (4.4) | 2, 3 |
| 2 | 53.9 CH | 3.98, dd (4.4, 2) | 1, 3, 1' |
| 3 | 71.4 CH | 4.05, dd (2, 6.4) | 2, 4 |
| 4 | 70.6 CH | 5.26, dt (6.4, 3) | 3, 5, 1'' |
| 5-a 5-b | 61.9 CH2 | 4.19, dd (12, 3) 4.46, dd (12, 3) | 4, 1''' |
| 1' 1'' 1''' 1'''' | 173.2 qC 173.4 qC 173.8 qC 59.5 CH2 | 4.28, m | 1, 2'''' |
| 2' 2'' 2''' 2'''' | 33.3 CH2 36.1 CH2 33.3 CH2 66.3 CH2 | 2.36, t (7.5) 2.20, t (7.2) 2.35, t (7.5) 3.65, m | 1', 4' 1'', 4''' 1''', 3'''' |
| 3' 3'' 3''' 3'''' | 24.9 CH2 25.1 CH2 24.7 CH2 53.6 CH3 | 1.60, bs 1.63, m 1.71, m 1.69, bs 3.23, s | 1', 5' 1'', 5''' 1''', 5''' 2'''' |
| 4' 4'' 4''' | 29.6 CH2 26.9 CH2 29.6 CH2 | 1.32, bs 2.14, m 1.32, bs | 2', 6' 2'', 6''' 2''', 6''' |

TABLE 2-continued

Bathymodiolamide C(3) NMR data 600 MHz in CD3OD

| Position | $\delta_C$, mult. | $\delta_H$ (J in Hz) | HMBC[a] |
|---|---|---|---|
| 5' 5" 5''' | 29.6 CH2 129.9 CH2 29.6 CH2 | 1.32, bs 5.45, m 1.32, bs | 3', 7' 3", 7" 3''', 7''' |
| 6' 6" 6''' | 29.6 CH2 127.6 CH 29.6 CH2 | 1.32, bs 5.35, m 1.32, bs | 4', 8' 4", 8" 4''', 8''' |
| 7' 7" 7''' | 29.7 CH2 25.3 CH2 29.7 CH2 | 1.32, bs 2.86, m 1.32, bs | 5', 9' 5", 9" 5''', 9''' |
| 8' 8" 8''' | 29.7 CH2 127.5 CH 29.7 CH2 | 1.32, bs 5.40, m 1.32, bs | 6', 10' 6", 10" 6''', 10''' |
| 9' 9" 9''' | 29.7 CH2 129.5 CH 29.7 CH2 | 1.32, bs 5.36, m 1.32, bs | 7', 11' 7", 11" 7''', 11''' |
| 10' 10" 10''' | 29.7 CH2 25.3 CH2 29.7 CH2 | 1.32, bs 2.85, m 1.32, bs | 8', 12' 8", 12" 8''', 12''' |
| 11' 11" 11''' | 29.5 CH2 129.5 CH 29.5 CH2 | 1.32, bs 5.39, m 1.32, bs | 9', 13' 9", 13" 9''', 13''' |
| 12' 12" 12''' | 29.5 CH3 128.0 CH 29.5 CH2 | 1.32, bs, 5.39, m 1.32, bs | 10', 14' 10", 14" 10''', 14''' |
| 13' 13" 13''' | 29.5 CH2 25.3 CH2 29.5 CH2 | 1.32, bs 2.84, m 1.32, bs | 11', 15' 11", 15" 11''', 15''' |
| 14' 14" 14''' | 29.5 CH2 128.5 CH 29.4 CH2 | 1.32, bs 5.38, m 1.32, bs | 12', 16' 12", 16" 12''', 16''' |
| 15' 15" 15''' | 29.5 CH2 129.2 CH 28.9 CH2 | 1.32, bs 5.38, m 1.32, bs | 13', 17' 13", 17" 13''', 16''' |
| 16' 16" 16''' | 29.5 CH2 25.3 CH2 13.2 CH3 | 1.32, bs 2.84, m 0.92, t (7.5) | 14', 18' 14", 18" 14''', 15''' |
| 17' 17" | 29.5 CH2 129.2 CH | 1.32, bs 5.35, m | 15', 19' 15", 19" |
| 18' 18" | 29.5 CH2 128.6 CH | 1.32, bs 5.36, m | 16', 20' 16", 20" |
| 19' 19" | 29.5 CH2 27.4 CH2 | 1.32, bs 2.08, m | 17', 21' 17", 21" |
| 20' 20" | 29.0 CH2 22.6 CH2 | 1.32, bs 1.35, m | 18', 21' 18", 21" |
| 21' 21" | 13.2 CH3 13.3 CH3 | 0.91, t (7.5) 0.93, t (7.5) | 19', 20' 19", 20" |

TABLE 3

Bathymodiolamide D(4) NMR data 600 MHz in CD3OD

| Position | $\delta_C$, mult. | $\delta_H$ (J in Hz) | HMBC[a] |
|---|---|---|---|
| 1-a 1-b | 63.3 CH2 | 4.00, d (4.4) 4.00, d (4.4) | 2, 3 |
| 2 | 53.9 CH | 3.98, dd (4.4, 2) | 1, 3, 1' |
| 3 | 71.2 CH | 4.05, dd (2, 6.4) | 2, 4 |
| 4 | 70.6 CH | 5.26, dt (6.4, 3) | 3, 5, 1" |
| 5-a 5-b | 61.9 CH2 | 4.19, dd (12, 3) 4.46, dd (12, 3) | 4, 1''' |
| 1' 1" 1''' 1'''' | 173.2 qC 173.4 qC 173.8 qC 69.5 CH2 | 4.28, m | 1, 2''' |
| 2' 2" 2''' 2'''' | 30.0 CH2 30.1 CH2 30.2 CH2 66.3 CH2 | 2.33, t (7.5) 2.20, t (7.2) 2.33, t (7.5) 3.65, m | 1', 4' 1", 4" 1''', 4''' 1'''', 3'''' |
| 3' 3" 3''' 3'''' | 24.9 CH2 25.5 CH2 24.6 CH2 53.6 CH3 | 1.60, bs 1.63, m 1.69, bs 3.23, s | 1', 5' 1", 5" 1''', 5''' 2'''' |
| 4' 4" 4''' | 29.8 CH2 31.7 CH2 29.8 CH2 | 1.32, bs 2.05, m 1.32, bs | 2', 6' 2", 6" 2''', 6''' |
| 5' 5" 5''' | 29.8 CH2 129.5 CH 29.8 CH2 | 1.32, bs 5.38, m 1.32, bs | 3', 7' 3", 7" 3''', 7''' |
| 6' 6" 6''' | 29.8 CH2 129.5 CH 29.8 CH2 | 1.32, bs 5.38, m 1.32, bs | 4', 8' 4", 8" 4''', 8''' |
| 7' 7" 7''' | 29.7 CH2 26.5 CH2 29.7 CH2 | 1.32, bs 2.81, m 1.32, bs | 5', 9' 5", 9" 5''', 9''' |
| 8' 8" 8''' | 29.7 CH2 127.9 CH 29.7 CH2 | 1.32, bs 5.38, m 1.32, bs | 6', 10' 6", 10" 6''', 10''' |
| 9' 9" 9''' | 29.5 CH2 129.5 CH 29.6 CH2 | 1.32, bs 5.38, m 1.32, bs | 7', 11' 7", 11" 7''', 11''' |
| 10' 10" 10''' | 29.5 CH2 26.9 CH2 29.6 CH2 | 1.32, bs 2.05, m 1.32, bs | 8', 12' 8", 12" 8''', 12''' |
| 11' 11" 11''' | 28.9 CH2 26.5 CH2 29.5 CH2 | 1.32, bs 1.40, m 1.32, bs | 9', 12' 10", 12" 10''', 13''' |
| 12' 12" 12''' | 13.2 CH3 13.1 CH3 29.5 CH2 | 0.89, t (7.0) 0.91, t (7.5) 1.32, bs | 10', 11' 10", 11" 11''', 13''' |
| 13''' | 28.9 CH2 | 1.32, bs | 12''', 14''' |
| 14''' | 13.0 CH3 | 0.90, t (7.5) | 12''', 13''' |

45

TABLE 4

Bathymodiolamide E(5) NMR data 600 MHz in CD3OD

| Position | $\delta_C$, mult. | $\delta_H$ (J in Hz) | HMBC[a] |
|---|---|---|---|
| 1-a 1-b | 63.3 CH$_2$ | 4.00, d (4.4) 4.00, d (4.4) | 2, 3 |
| 2 | 53.9 CH | 3.98, dd (4.4, 2) | 1, 3, 1' |
| 3 | 71.4 CH | 4.05, dd (2, 6.4) | 2, 4 |
| 4 | 70.6 CH | 5.26, dt (6.4, 3) | 3, 5, 1" |
| 5-a 5-b | 61.9 CH$_2$ | 4.19, dd (12, 3) 4.46, dd (12, 3) | 4, 1''' |
| 1' 1" 1''' 1'''' | 173.2 qC 173.4 qC 173.8 qC 59.5 CH$_2$ | 4.28, m | |
| 2' 2" 2''' 2'''' | 33.6 CH$_2$ 36.1 CH$_2$ 24.3 CH$_2$ 66.3 CH$_2$ | 2.35, t (7.5) 2.20, t (7.2) 1.98, m 2.00, m 3.65, m | 1', 4' 1", 4" 1''', 4''' |
| 3' 3" 3''' 3'''' | 26.7 CH$_2$ 36.2 CH$_2$ 35.4 CH 60.9 CH$_2$ | 1.58, m 2.18, m 3.14, m 3.71, d(6) | 1', 5' 1", 5" 1''', 5''' |
| 4' 4" 4''' 4'''' | 29.6 CH$_2$ 129.5 CH 71.7 CH 60.9 CH$_2$ | 1.32, bs 5.38, m 4.07, m 3.71, d(6) | 2', 6' 2", 6" 2''', 6''' |
| 5' 5" 5''' 5'''' | 29.6 CH$_2$ 127.6 CH 129.6 CH 53.4 CH3 | 1.32, bs 5.38, m 5.48, dd (18, 6) 3.25, s | 3', 7' 3", 7" 3''', 7''' 4'''' |
| 6' 6" 6''' | 29.6 CH$_2$ 25.3 CH$_2$ 133.5 CH | 1.32, bs 2.88, m 5.71, dd (18, 6) | 4', 8' 4", 8" 4''', 8''' |
| 7' 7" 7''' | 29.7 CH$_2$ 127.6 CH 32.1 CH$_2$ | 1.32, bs 5.38, m 2.08, m | 5', 9' 5", 9" 5''', 9''' |
| 8' 8" 8''' | 29.7 CH$_2$ 129.5 CH 29.7 CH$_2$ | 1.32, bs 5.38, m 1.32, bs | 6', 10' 6", 10" 6''', 10''' |
| 9' 9" 9''' | 29.7 CH$_2$ 25.3 CH$_2$ 29.6 CH$_2$ | 1.32, bs 2.86, m 1.32, bs | 7', 11' 7", 11" 7''', 11''' |
| 10' 10" 10''' | 29.7 CH$_2$ 128.1 CH 29.6 CH$_2$ | 1.32, bs 5.38, m 1.32, bs | 8', 12' 8", 12" 8''', 12''' |
| 11' 11" 11''' | 29.5 CH$_2$ 128.0 CH 29.5 CH$_2$ | 1.32, bs 5.38, m 1.32, bs | 9', 12' 9", 13" 9''', 13''' |
| 12' 12" 12''' | 29.5 CH$_2$ 25.3 CH$_2$ 29.5 CH$_2$ | 1.32, bs 2.84, m 1.32, bs | 10', 11' 10", 14" 10''', 14''' |

TABLE 4-continued

Bathymodiolamide E(5) NMR data 600 MHz in CD3OD

| Position | $\delta_C$, mult. | $\delta_H$ (J in Hz) | HMBC$^a$ |
|---|---|---|---|
| 13' 13" 13''' | 29.5 CH$_2$ 128.4 CH 29.5 CH$_2$ | 1.32, bs 5.38, m 1.32, bs | 11', 12' 11", 15" 11''', 15''' |
| 14' 14" 14''' | 29.5 CH$_2$ 129.2 CH 29.4 CH$_2$ | 1.32, bs 5.38, m 1.32, bs | 13', 15' 12", 16" 12''', 16''' |
| 15' 15" 15''' | 29.5 CH$_2$ 27.5 CH$_2$ 28.9 CH$_2$ | 1.32, bs 2.08, m 1.32, bs | 14', 16' 13", 16" 13''', 16''' |
| 16' 16" 16''' | 29.5 CH$_2$ 22.6 CH$_2$ 13.0 CH$_3$ | 1.32, bs 1.35, m 0.90, t (7.5) | 15', 17' 14", 15" 14''', 15''' |
| 17' 17" | 29.5 CH$_2$ 13.1 CH$_3$ | 1.32, bs 0.91, t (7.5) | 16', 18' 15", 16' |
| 18' | 29.5 CH$_2$ | 1.32, bs | 17', 19' |
| 19' | 29.5 CH$_2$ | 1.32, bs | 18', 20' |
| 20' | 29.0 CH$_2$ | 1.32, bs | 19', 21' |
| 21' | 13.2 CH$_3$ | 0.91, t (7.5) | 20', 19' |

Figure 1:
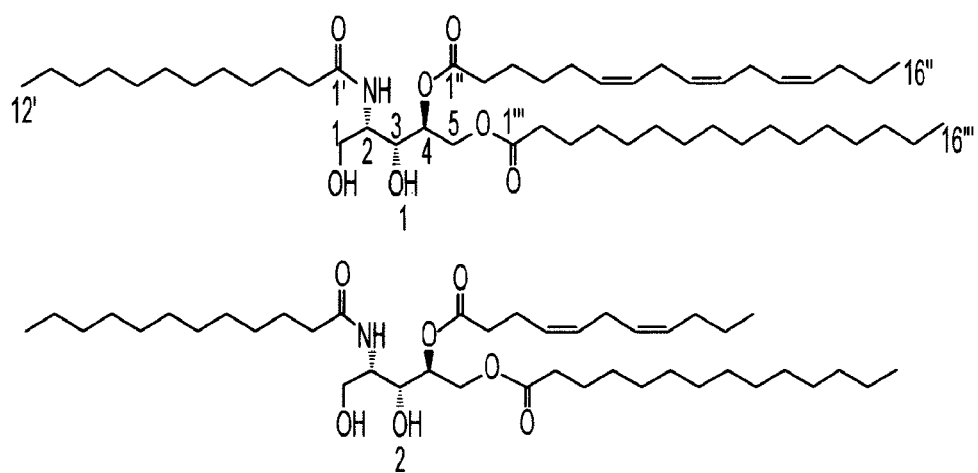
FIG. 1 shows the structures of bathymodiolamides A (1) and B (2).
Figure 2:
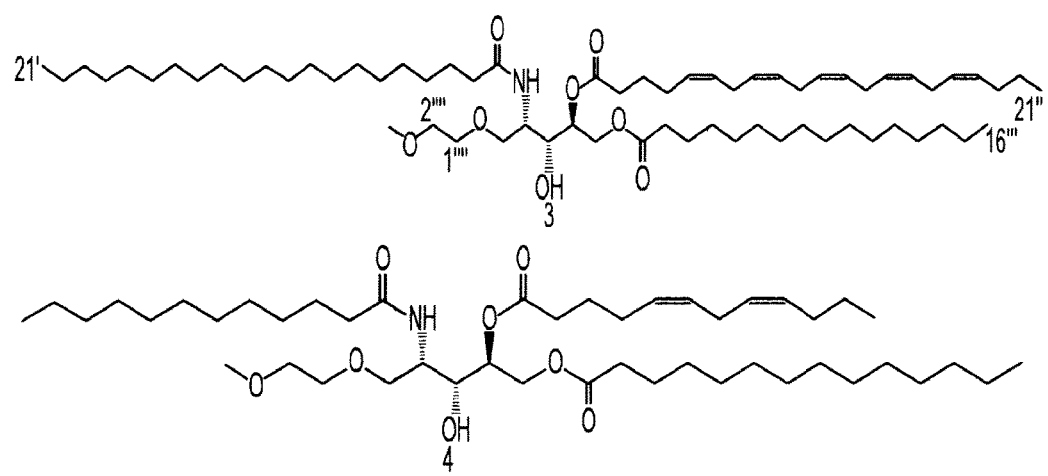
FIG. 2 shows the structures of bathymodiolamides C (3) and D (4).
Figure 3:
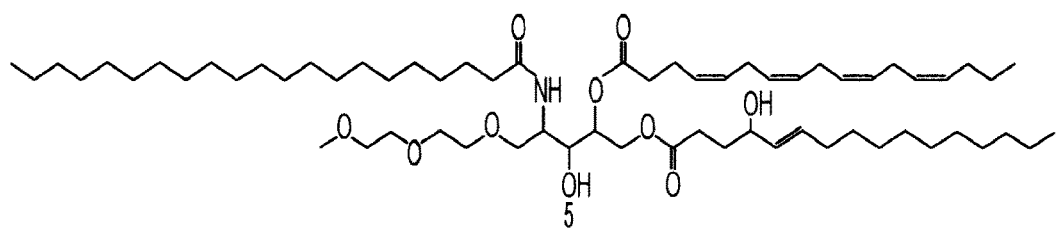
FIG. 3 shows the structure of bathymodiolamide E (5).
Figure 4:
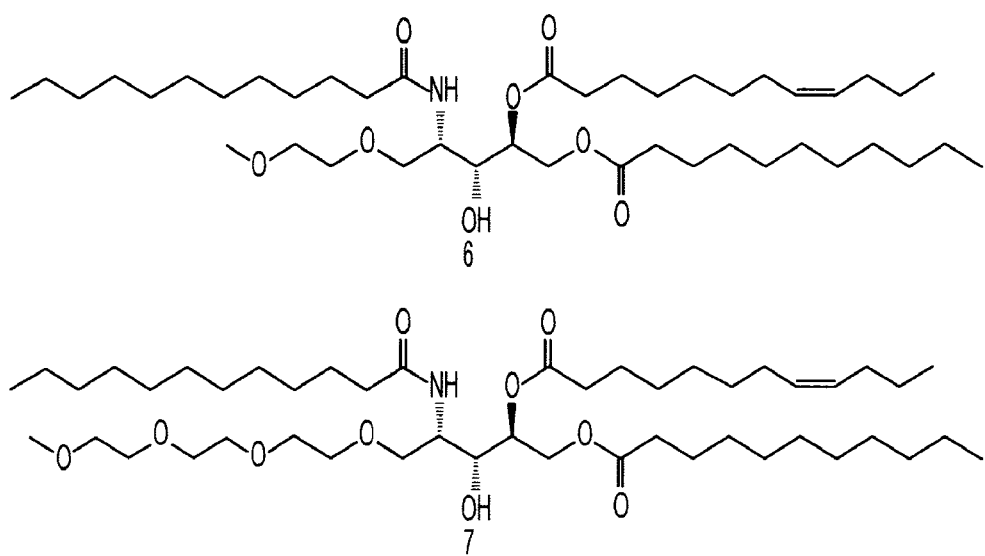
FIG. 4 shows the structures of bathymodiolamides F (6) and G (7).
Figure 5:
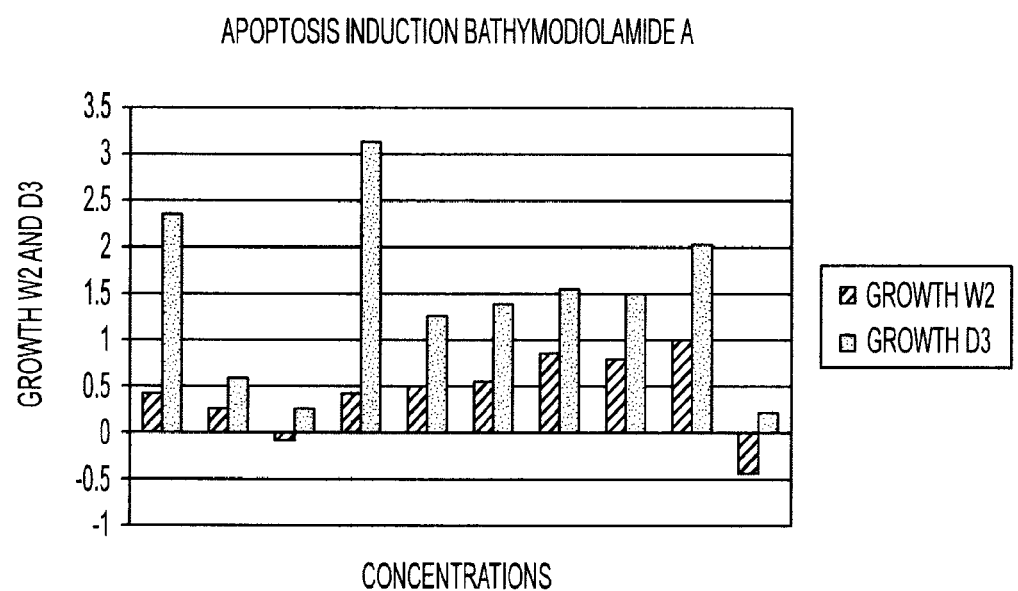
FIG. 5 shows data from an apoptosis induction assay for Bathymodiolamide A (1).
Figure 6:
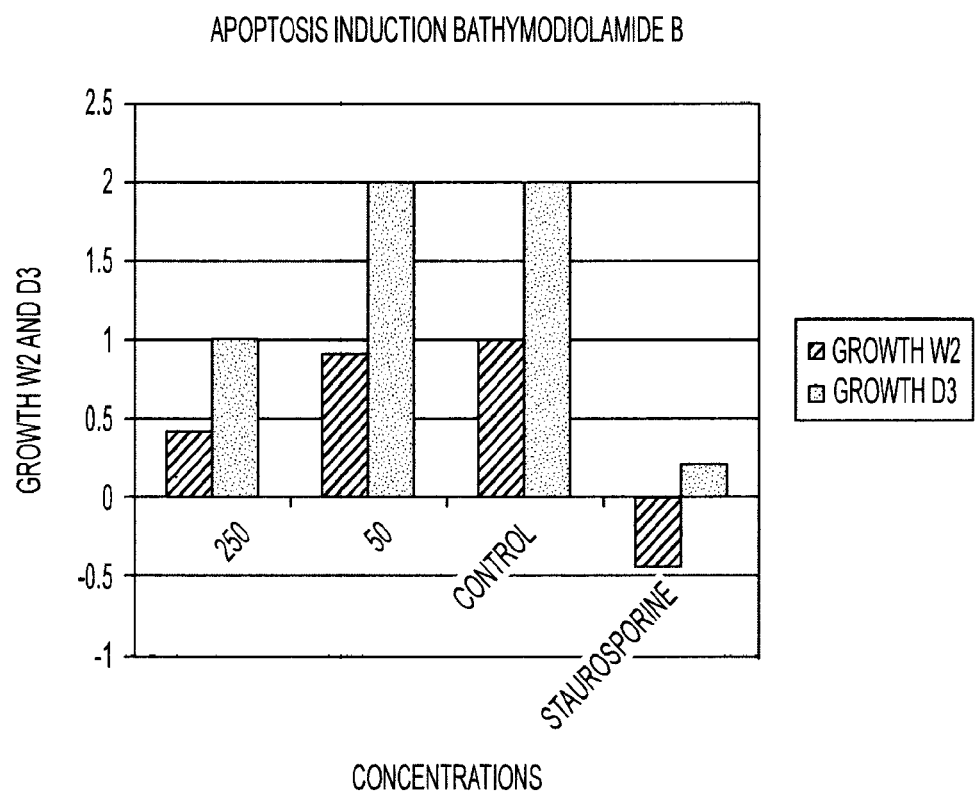
FIG. 6 shows data from an apoptosis induction assay for Bathymodiolamide B (2).
Figure 7:
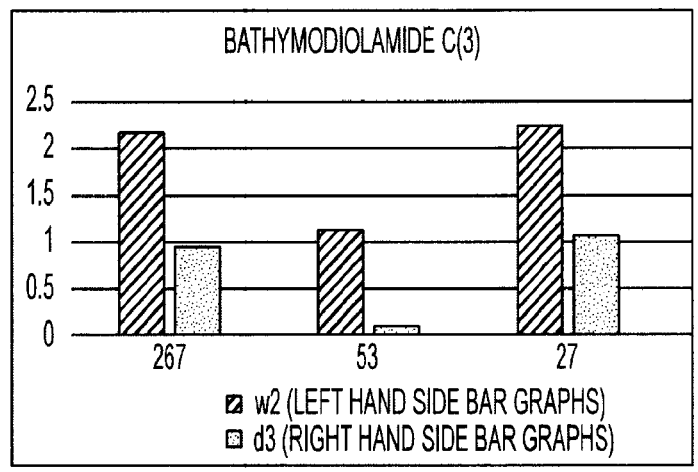
FIG. 7 shows data from an apoptosis induction assay for Bathymodiolamides C (3), D(4) and E(5).
Figure 7:
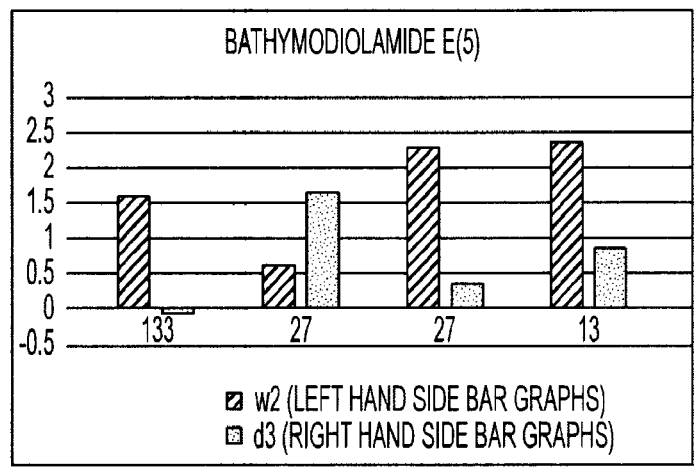
Figure 7:
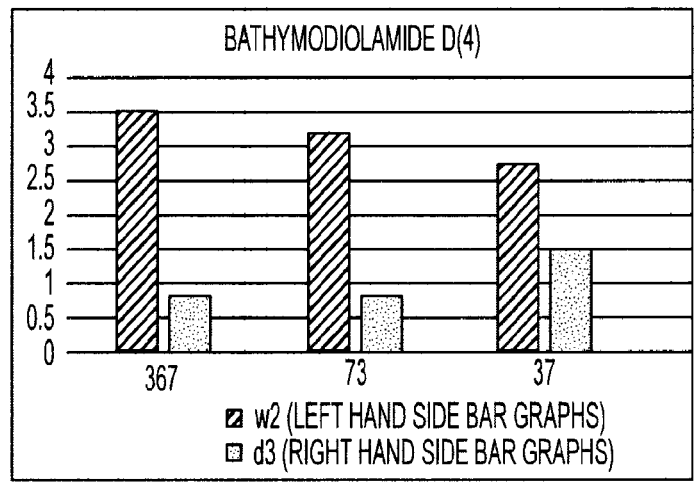
Figure 8:
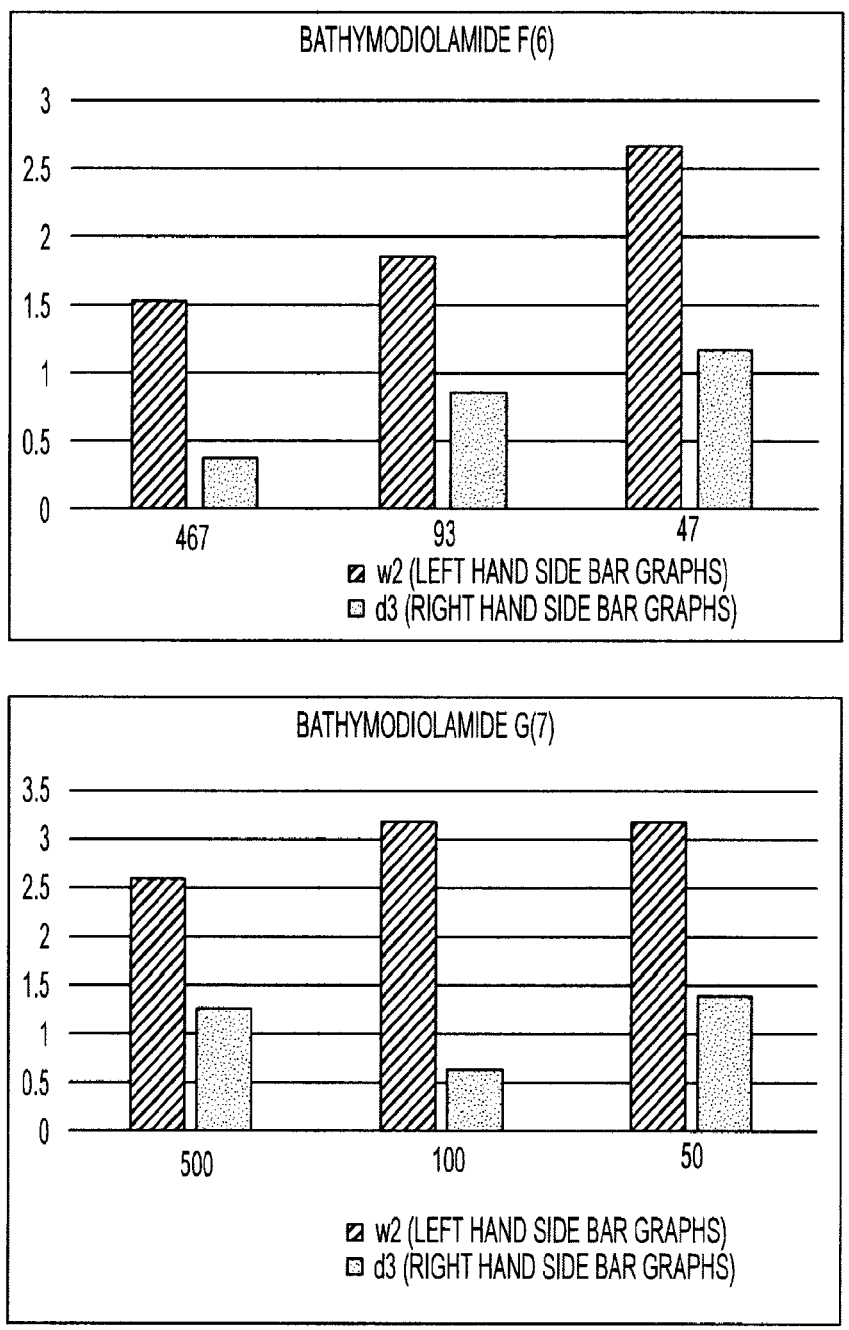
FIG. 8 shows data from an apoptosis induction assay for Bathymodiolamides F (6) and G(7).
Figure 9:
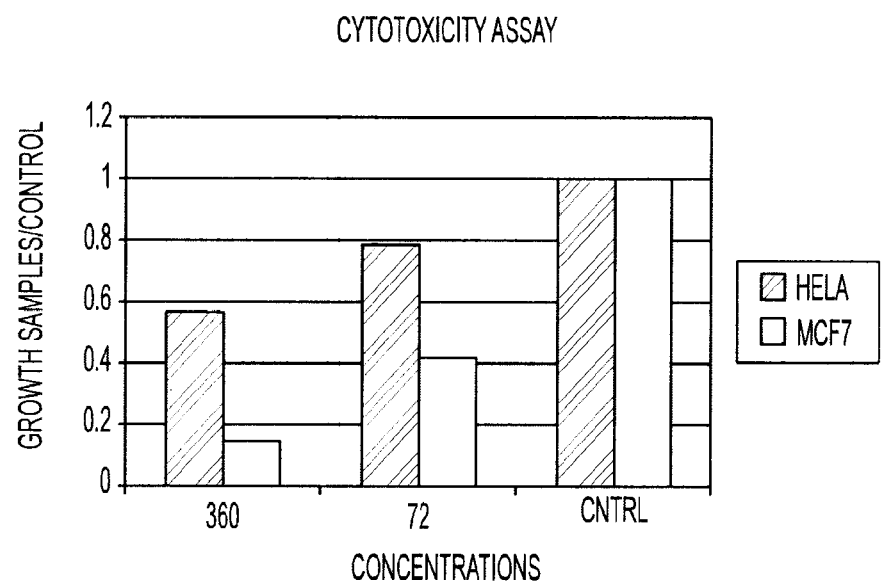
FIG. 9 shows data from a cytotoxicity assay for Bathymodiolamide A (1).
Figure 10:
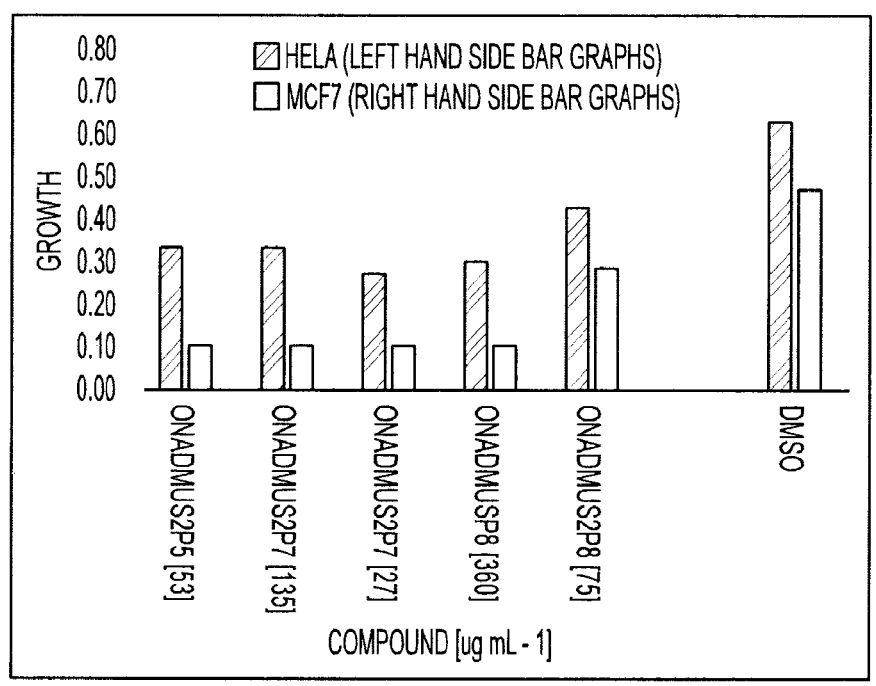
FIG. 10 shows data from a cytotoxicity assay for Bathymodiolamides C(3) and E(5) (ONADMUS2P5 and ONADMUS2P7).

The molecular formula of 1 was established as C$_{49}$H$_{89}$NO$_7$ on the basis of HRMALDITOFMS [m/z 804.6712 (M+H]$^+$. The 13C NMR spectrum for 1 clearly indicated resonances for three ester or amide carbonyl carbons ($\delta$C 173.2, 173.4, 173.8), as well as four oxygen-bearing carbons ($\delta$C 59.9, 62.5, 63.7, 66.1) and one nitrogen-bearing carbon ($\delta$C 53.5, $\delta$H 4.29). Analysis of the multiplicity-edited HSQC spectrum for 1 revealed that these heteroatom-substituted carbons comprise two methylenes (CH2-1, $\delta$C 63.7, $\delta$H 3.65; CH2-5, $\delta$C 59.9, $\delta$H5a 4.20, $\delta$H5b 4.45) and three methines (CH-2, $\delta$C 53.5, $\delta$H 4.29; CH-3, $\delta$C 62.5, $\delta$H 4.01; CH-4, $\delta$C 66.1, $\delta$H 5.25). The HMBC correlations between H-2 and the carbonyl at $\delta$C 173.2, H-4 and the carbonyl at $\delta$C 173.4, and H-5a and H-5b and the carbonyl at $\delta$C 173.8 suggested that 1 has an amide moiety attached to C-2 and two ester moieties attached to C-4 and C-5. Considering the molecular formula and all carbon signals for 1, the remaining oxygen bearing carbons C-1 and C-3 are substituted with hydroxy groups, resulting in primary and secondary alcohols at C-1 and C-3, respectively. The connectivity of C-1 through C-5 of 1 was established from COSY data as shown in FIG. 1, confirming the presence of the amino alcohol moiety in 1. The remaining partial structures for 1 could be assigned as three acyl moieties. Given the six degrees of unsaturation of 1 based on its molecular formula, three double bonds must be present in one or more of the three acyl moieties. The HMBC correlations from $\delta$H 5.35 to $\delta$C 26.5 and from $\delta$H 2.81 to $\delta$C 127.5, taken together with the 4H integral of the signal at $\delta$H 2.81 in the 1H NMR spectrum of 1, indicated the occurrence of four bis-allylic protons and two bis-allylic methylene carbons, suggesting that all three double bonds are located in one branch of the aliphatic side chain. Since bis-allylic carbon signals for Z and E isomers are observed at ca. $\delta$C 27 and 32, respectively, the 26.5 ppm shift suggested that all double bonds have a cis geometry (Z).

To deduce the identity of the fatty acids, 1 was subjected to a transesterification reaction in MeOH/NaOMe (2 h). After routine workup of the reaction, the nonpolar organic extract was analyzed by GC-MS and ESIMS, and three ion peaks [M+H]$^+$ at m/z 215.2010, 265.2166, and 271.2636 were observed, corresponding to dodecanoic acid methyl ester, hexadecatrienoic acid methyl ester, and hexadecanoic acid methyl ester, respectively. The regiochemical distribution of these three acyl chains was established using different ionization mass spectrometry analyses. The amide bond was most readily recognized by MALDITOFMS/MS [M+H]$^+$ at m/z 184.1, corresponding to the cleavage of the dodecanoyl moiety. ESIMS was used to differentiate the acyl attached at C-4 and C-5. Fragmentation by positive-mode ESIMS generated a more stable fragment ion from cleavage of the acyl chain attached at C-5 than cleavage of the acyl chain attached to C-4. In contrast, the negative-mode ESIMS fragment ion resulting from cleavage of the acyl chain attached at C-4 is more stable. Successive losses of dodecanoyl and hexadecatrienoyl moieties were observed in the negative-mode ESIMS (m/z 584.2 and 367.1, respectively). From these analyses it was concluded that the dodecanoyl moiety is attached to C-2, while the hexadecatrienoyl and hexadecanoyl moieties are attached to C-4 and C-5, respectively. To verify this conclusion, a selective enzyme reaction was performed. Upon regioselective enzymic hydrolysis of 1 with lipase enzyme type III in dioxane/H2O (1:1) at 37° C. for 4 hours, only hexadecanoic acid was obtained, as evidenced by ESIMS and comparison with an authentic sample. Thus, it was concluded that the hexadecanoyl residue is attached to C-5 of 1. The aqueous phase from the hydrolysis product of 1 yielded an aminotetraol, which was identified as (2S,3S,4R)-2-amino-1,3,4,5-pentane tetraol. The relative configuration of the aminotetraol was elucidated using the $^3J_{H,H}$ coupling constant analysis from an NMR database for a given stereocluster. Eight stereoisomeres are possible for aminotetraol, depending on the relative position of H-2 and H-3 (S=syn or A=anti) and H-3 and H-4 (S=syn or A=anti), and the eight isomers are classified as follows: one pair of SS, one pair AA, one pair of SA, and one pair of AS. According to the value recorded for aminotetraol of the $^3J_{H,H}$ coupling constant between H-2 and H-3 (J=2.5 Hz) and H-3 and H-4 (J=7 Hz), H-2 and H-3 are on the same side (S=syn) and H-3 and H-4 are on the opposite side (A=anti); thus the remaining probable stereoisomers is the pair of SA: (2S,3S,4R)-2-amino-1,3,4,5-pentane tetraol and (2R,3R,4S)-2-amino-1,3,4,5pentane tetraol. Theoretically these two isomers should have opposite optical rotation sign. The positive optical rotation of aminotetraol ([α]$^{24}_D$+8 (c 0.05, H$_2$O)) favors the (2S,3S,4R)-2-amino-1,3,4,5-pentane tetraol configuration as that of seen in L-arabino-phytosphingosine ([α]$^{25}_D$+5 (c 0.51, pyridine)), which is also the opposite of that observed in D-arabinophytosphingosine ([α]$^{25}_D$−4.3 (c 0.50, pyridine)). The identical coupling constants between H-2 and H-3 (J=3 Hz) and H-3 and H-4 (J=6 Hz) along with the optical rotation reported ([α]$^{27}_D$+9.2 (c 0.05, MeOH)) for the sphingosine derivative and bathymodiolamides A (1) further suggested a (2S,3S,4R)-configuration of the sphingosine-like moiety in 1. From the above data, the structure of 1 was established as shown.

The molecular formula of 2 was established as C$_{42}$H$_{77}$NO$_7$ on the basis of HRMALDITOFMS (m/z 730.5594 [M+Na]+). The strong similarity of its $^1$H NMR spectrum to that of bathymodiolamide A (1) revealed that 1 and 2 share the same general structural features. Upon regioselective enzymic hydrolysis of 2 with lipase enzyme type III in dioxane/H2O (1:1) at 37° C. for 4 hours, 10 only tetradecanoic acid was obtained, as established by ESIMS analysis and comparison with an authentic sample. Thus, it was concluded that the tetradecanoyl residue is attached to the C-5 position of 2. The hydrolysis of 2 gave similar results to those observed for 1, with the exception of the presence of undecadienoic acid methyl ester and tetradecanoic acid methyl ester. The structure of 2 is similar to 1 with undecadienoyl and tetradecanoyl residues at C-4 and C-5, respectively. Thus, the structure of 2 was established as shown.

The molecular formula of bathymodiolamide C(3) was established as $C_{66}H_{119}NO_8$ on the basis of HRMALDITOFMS (m/z 1054.8998 [M+H]+). The strong similarity of its $^1H$ NMR spectrum to that of bathymodiolamides A (1) and B (2) revealed that 1, 2 and 3 share the same general structural features. The striking difference is the presence of two signals at δ3.65 and δ4.28 attached to carbons δ66.30 and δ59.52 respectively.

Analyses of multiplicity edited HSQC and COSY revealed that these two signals belong to two adjacent methylene groups, furthermore, these two methylenes are characteristic of oxygen bearing carbon. HMBC correlations revealed that a methoxy group is attached to the carbon at 866.30 and the other carbon at 659.52 is attached to C-1 by an ether bond. This suggested that one methoxy ethylene group is attached to C-1 by an ether bond in the structure of 3. Upon regioselective enzymic hydrolysis of 3 with lipase enzyme type III in dioxane/$H_2O$ (1:1) at 37° C. for 4 h, only pentadecanoic acid was obtained, as established by ESIMS analysis and comparison with an authentic sample. Thus, it was concluded that the pentadecanoyl residue is attached to the C-5 position of 3. The hydrolysis of 3 revealed the presence of heneicosapentaenoic acid methyl ester and decosanoic acid methyl ester as well as pentadecanoic acid methyl ester. The residue attached to C-2 and having the amide bond was deduced by MALDITOFMS/MS (m/z 325.3563 [M+2H]+), corresponding to the cleavage of the heneicosanoyl moiety. The structure of 3 is similar to 1 and 2 with heneicosapentaenoyl and hexadecanoyl residues at C-4 and C-5, respectively. The coupling constant patterns of 1, 2 and 3 are very similar so it was concluded that the relative stereochemistry of 3 is (2S,3S,4R). Since bis-allylic carbon signals for Z and E isomers are observed at ca. δC 27 and 32, respectively, the 25.3 ppm shift suggested that all double bonds have a cis geometry (Z) (all-cis-5,8,11,14,17 heneicosapentaenoic acid for C-4) in the structure of 3. Thus, the structure of bathymodiolamide C(3) was established as shown.

The molecular formula of bathymodiolamide D(4) was established as $C_{46}H_{85}NO_8$ on the basis of HRMALDITOFMS (m/z 780.6340 [M+H]+). $^1H$ NMR and $^{13}C$ NMR of 4 are strongly similar to that of bathymodiolamide B(2). The two carbons at δ66.30 and δ59.52 are similar to that of seen in bathymodiolamide C(3). Multiplicity edited HSQC suggested that these two carbons are methylene groups. The protons at δ3.65 and δ4.28 are attached to δ66.30 and δ59.52 respectively. COSY correlation showed that these protons are adjacent. HMBC correlations revealed that a methoxy group is attached to the carbon at δ66.30 and the other carbon at δ59.52 is attached to C-1 by an ether bond as that of seen in 3. It was concluded that the structure of 4 is similar to 2 but with an incorporation of one methoxy ethylene group which is attached to C-1 by an ether bond. The other difference is the identity of the polyunsaturated fatty acid residue attached to C-4. The hydrolysis of 4 gave similar results to those observed for 2, with the exception of the presence of dodecadienoic acid methyl ester instead of undecadienoic acid methyl ester. Regioselective enzymic hydrolysis of 4 revealed that only tetradecanoic acid was obtained. Thus, it was concluded that the tetradecanoyl residue is attached to the C-5 position of 4. The residue attached to C-2 and having the amide bond was deduced by MALDITOFMS/MS (m/z 184.1 [M+H]+), corresponding to the cleavage of the dodecanoyl moiety. The dodecadienoyl residue was then assigned to be attached to C-2. The structure of 4 is established as shown.

The molecular formula of bathymodiolamide E(5) was established as $C_{64}H_{115}NO_{10}$ on the basis of HRMALDITOFMS (m/z 1080.8408 [M+Na]+). The proton NMR of 5 is very similar to that of 3 with the striking difference at the olefinic region. Two signals, at δH 5.48 and δH 5.71 which are attached to two olifenic carbons δC 129.61 and δC 133.57 respectively, are present in the NMR spectra of 5. COSY correlation revealed that these protons are adjacent. The coupling constant of J=18 Hz suggested that these two protons belong to a double bond in a trans position. The proton at δH 5.48 also shows COSY correlation to a proton at δH 4.07 which is attached to an oxygen bearing carbon δC 71.7. This oxygen bearing carbon is characteristic of a methine signal with an alcohol group. Thus, it was concluded that 5 has an hydroxy unsaturated fatty acid residue in its structural feature. Another striking difference between the NMR spectra of 5 and 3 is the presence of methylene carbon at δC 60.97 which is also a characteristic of oxygen bearing carbon. The methylene protons attached to this carbon exhibit signal at δH 3.71. Comparison of the proton signal integration of δH 3.71 and δH 3.65 indicated that the $CH_2$ at δC 60.97 represents not only one but two oxygen bearing carbons. HMBC correlation shows that these proton signals are correlated to the carbon of the terminal methoxy group at δC 53.39. Hence, the structure of 5 has one more ethylene glycol moiety in its structure compared to 3. The residue attached to C-2 and having the amide bond was deduced by MALDITOFMS/MS (m/z 325.3563 [M+2H]+), corresponding to the cleavage of the heneicosanoyl moiety. Regioselective enzymic hydrolysis of 5 revealed that only 4-hydroxy trans-5-hexadecaenoic acid was obtained, suggesting that 4-hydroxy trans-5-hexadecaenoyl residue is attached to C-5 position of 5. The hydrolysis of 5 gave heneicosanoic acid methyl ester, 4-hydroxy trans-5-hexadecaenoic acid methyl ester and heptadecatetraenoic acid methyl ester. Consequently, heptadecatetraenoyl residue is attached to C-4 position in 5. Bis-allylic carbon signals of heptadecatetraenoyl residue are observed at 25.3 ppm shift suggested that all double bonds of this residue have a cis geometry (Z) (all-cis-4,7,10,13-heptadecatetraenoic acid). The structure of 5 is established as shown.

Figure 15:
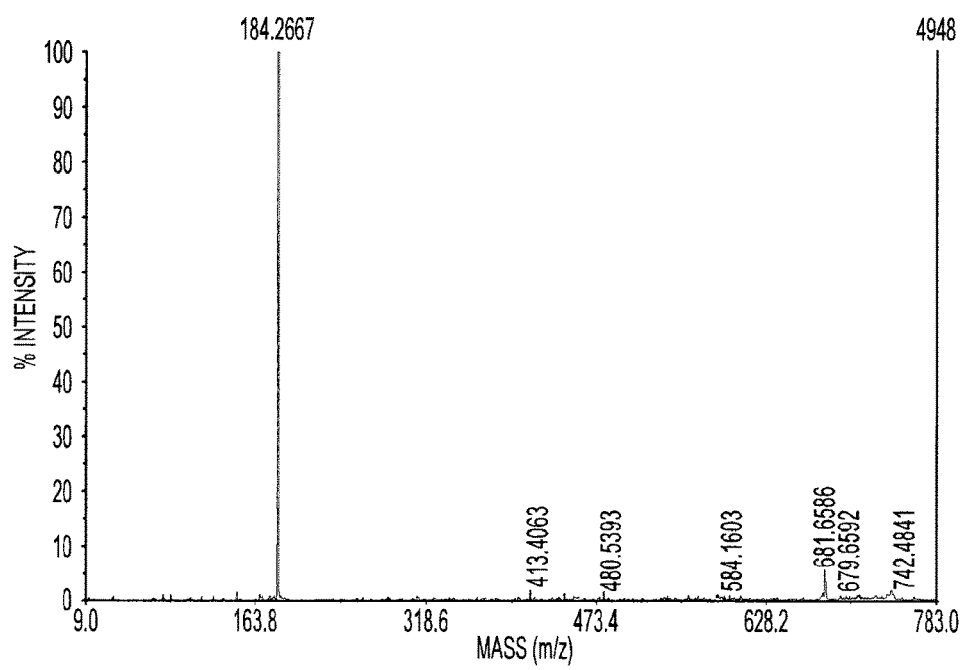
FIG. 15 shows MSMS of m/z 740.58 of bathymodiolamide F(6).
Figure 16:
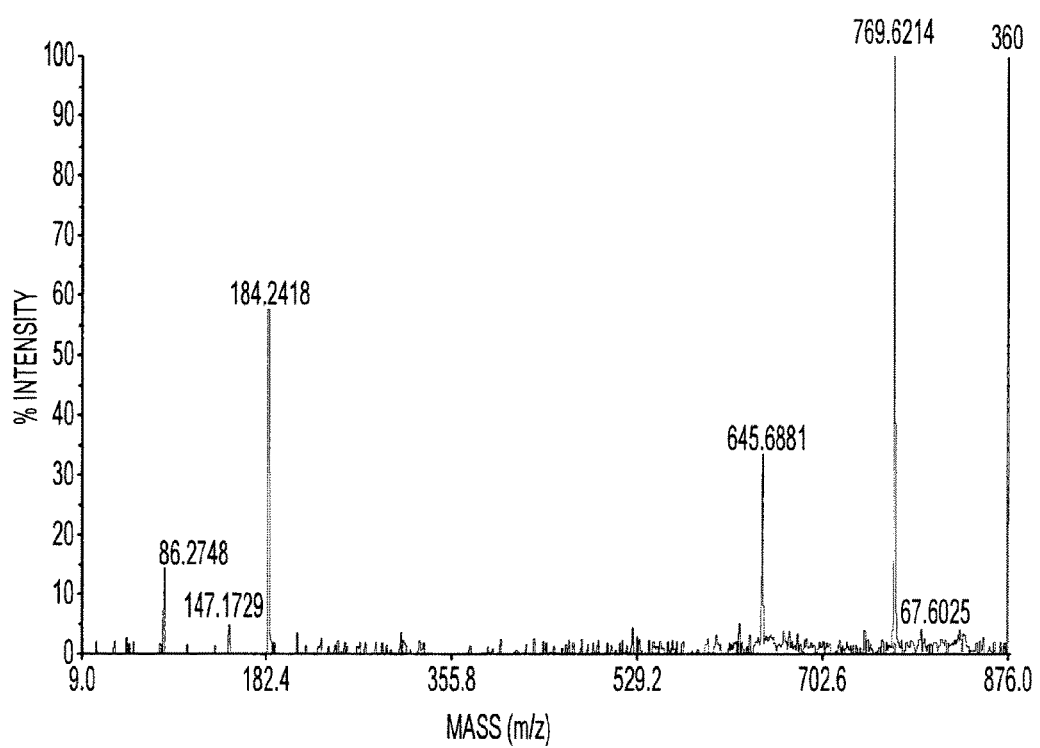
FIG. 16 shows MSMS of m/z 828.58 of bathymodiolamide G(7).

MSMS of the peak at m/z 740.58 and 828.58 of bathymodiolamide F(6) and bathymodiolamide G(7) displayed similar fragments (FIG. 15, 16) and easily identified as the cleavage of the dodecanoyl moiety which is attached to C-2 by an amide bond for both compounds. It was also found that dodecaenoyl and undecanoyl moieties are attached to C-4 and C-5, respectively. These compounds differ from their molecular weight with 88 mass unit corresponding to two ethylene glycol moieties $C_4H_8O_2$. Hence, the structure of 6 and 7 are similar except that 7 has two more ethylene glycol moieties on its structure. The structures of 6 and 7 are established as shown.

Example 2. Choice of Necrosis Inducers

Biological Evaluation (Apoptosis Induction). Testing for induction of apoptosis in the presence of bathimodiolamides A(1), B(2), C(3), D(4), E(5), F(6) and G(7) was carried out as described in Andrianasolo et al. using the ApoScreen assay. In this assay, the viability of treated W2 (apoptosis competent) and D3 (apoptosis defective) cells is measured using a modification of the MTT assay. For the current study, viability was measured at 0 and 48 h and differential growth was calculated in the presence and absence of the compounds. Staurosporine (an apoptosis inducer) was used as a positive control, and DMSO as a negative control. Bathymodiolamides did not induce apoptosis (see FIGS. 5, 6, 7, and 8).

Cytotoxicity Assay. Two cancer cell lines were used to demonstrate the inhibitory effect on cell growth of Bathymodiolamides. Cells were treated with varying concentrations of compounds. The $IC_{50}$ were measured. All compounds were shown to kill or inhibit the growth of the two cancer cell lines (HELA and MCF7). Since bathymodiolamides did not induce apoptosis they should affect the cell via non apoptotic pathway. In order to verify that assumption an LDH (Lactate Dehydrogenase) assay was performed.

LDH Assay of Bathymodiolamides C(3) and E(5)

Necrosis is accompanied by mitochondrial swelling and increased plasma membrane permeability. LDH is a soluble cytosolic enzyme that is released into the culture medium following loss of membrane integrity resulting from necrosis. LDH activity, therefore, can be detected and used as an indicator of cell membrane integrity and serves as a general means to assess necrosis.

Bathymodiolamides C(3) and E(5) were dissolved in DMSO in 5 mM stock. Hydrogen peroxide ($H_2O_2$) was obtained from EMD Millipore (Catalog# M1072980250). Pierce LDH Cytotoxicity Assay Kit was obtained from Thermo Scientific (Catalog#88953). MCF7 human breast cancer cell line was obtained from American Type Culture Collection (Manassas, Va.). MCF7 cells were grown in EMEM medium supplemented with 10% heat-inactivated fetal bovine serum, 10 µg/ml bovine insulin, 100 µg/ml of penicillin, and 100 µg/ml of streptomycin. Cultures were maintained at 37° C. in a humidified atmosphere of 5% $CO_2$ and 95% air.

Assay Procedure:

a. 20000 of MCF7 cells/well in 100 µl of 10% FBS culture medium in triplicate wells were seeded in a 96-well plate in an incubator at 37° C., 5% $CO_2$ for overnight incubation.

b. The next day, the culture medium was replaced with fresh medium containing 1% FBS medium.

c. 5 doses of compound 3 or 4 at 10 µM, 50 M, 100 µM, 150 µM, 200 µM, 0.1% $H_2O_2$, or 4% DMSO were added to the triplicate wells containing cells and incubated at 37° C., 5% $CO_2$ for 3 hours.

d. 10 µl of 10× lysis buffer was added to triplicate wells containing cells and incubated at 37° C., 5% $CO_2$ for 45 minutes.

e. 50 µl of each sample medium was transferred to a 96-well flat-bottom plate in triplicate wells.

f. 50 µl of Reaction Mixture was transferred to each sample well and mixed by gentle shaking.

g. The plate was incubated at room temperature for 30 minutes protected from light.

h. The absorbance at 492 nm was measured immediately using an Envision 2104 Multilabel Reader (PerkinElmer, Santa Clara, Calif.).

i. The LDH release (%) was calculated using the formula:

LDH release (%)=(Compound treated sample LDH activity-DMSO treated sample LDH activity)×100/(10×Lysis buffer treated sample LDH activity-DMSO treated sample LDH activity)

j. LDH release histogram graphs were plotted using the GraphPad Prism 4 program.

Figure 11:
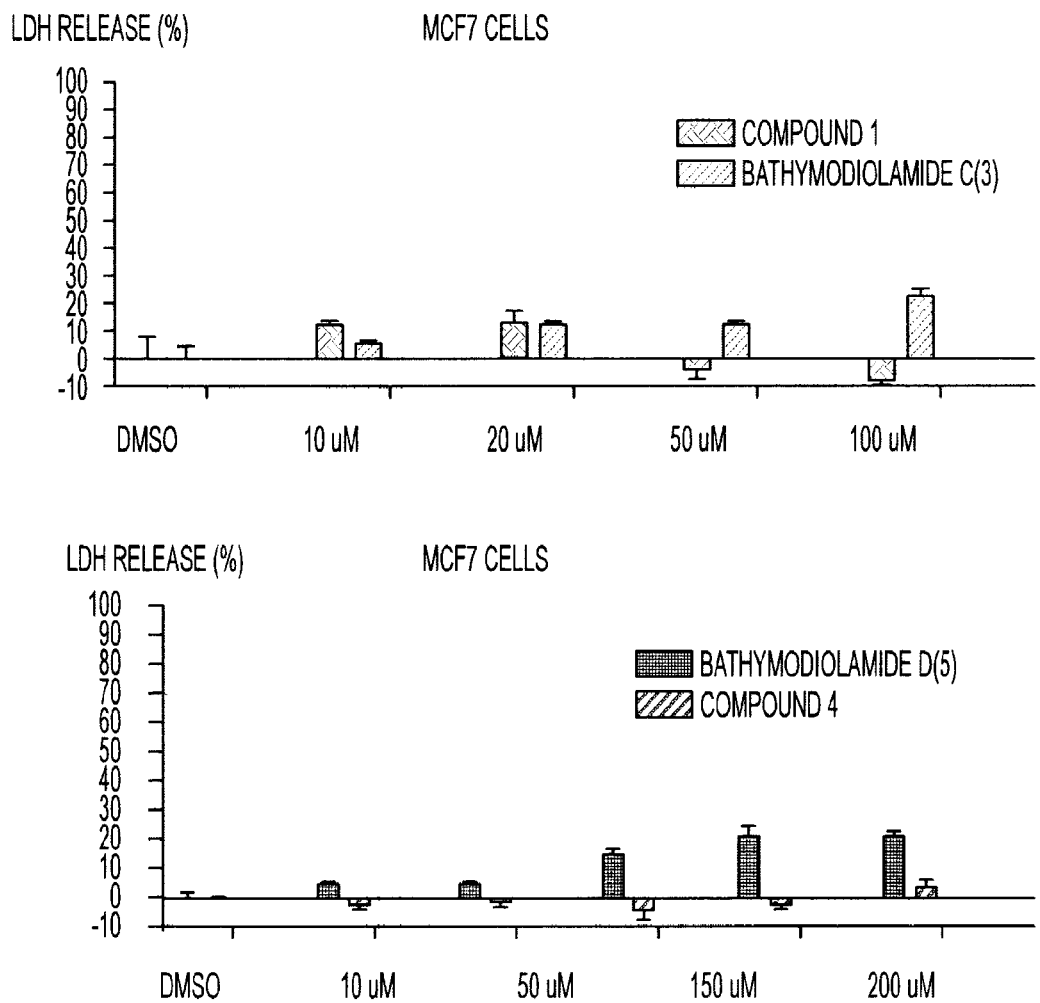
FIG. 11 shows LDH release data for Bathymodiolamides C(3) and D(5).
Figure 12:
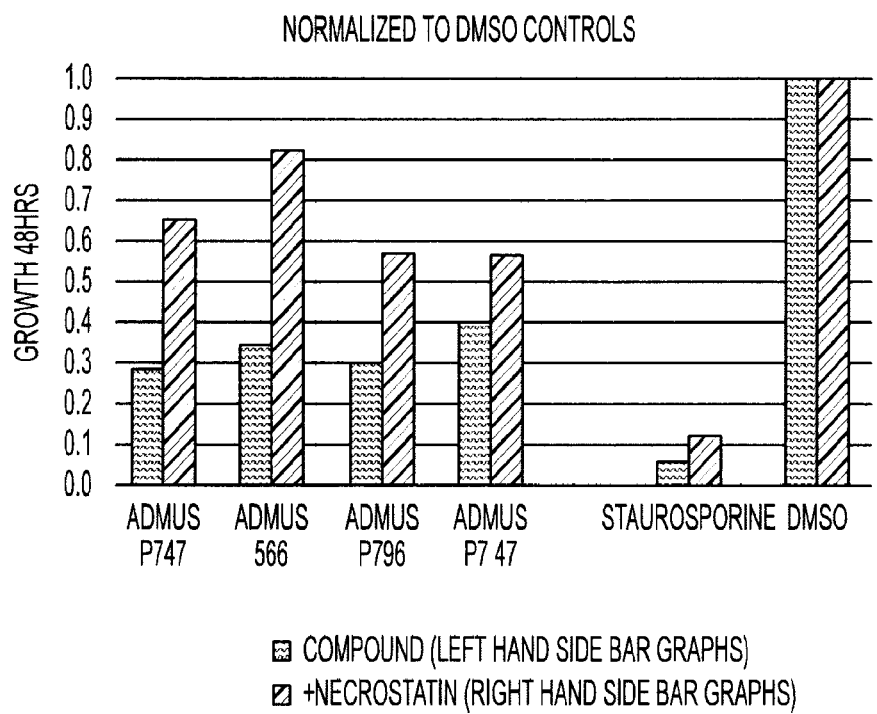
FIG. 12 shows data from the treatment of Bax and Bak null cells (D3) with Bathymodiolamide C(3) (ADMUS P5), Bathymodiolamide E(5) (ADMUS P7) and necrostatin.

Lactate Dehydrogenase (LDH) assay results revealed that the test compounds induce necrosis (FIG. 11).

Example 3. Co-Addition of Necrostatin and Bathymodiolamide C(3) or Bathymodiolamide E(5) to Bax and Bak Null Cells (D3)

D3 is an immortal epithelial cell lines genetically deleted for Bax and Bak. Apoptosis cannot be restored in these cells. W2 cells (wild-type) have apoptosis function intact. W2 and D3 cell lines are used in screening for compounds that promote apoptosis by the criteria of killing W2 and not D3 cells. This screen should identify compounds that have the capacity to activate apoptosis upstream of, and that require Bax and Bak.

Both cell lines were tested with bathymodiolamides C(3) and D(5). A decreased growth rate was measured for D3 cells in the presence of the either compound. Growth of W2 was not affected. The results indicate that the compounds do not induce apoptosis but may induce a different kind of cell death.

To test whether necroptosis was induced in the presence of the compounds, D3 cells were incubated with bathymodiolamides C(3) and D(5) (66, 132 ug mL-1 (3), 47, 95 ug mL-1 (5)) with addition of 30 uM necrostatin, a necroptosis, a known inhibitor of necroptosis.

In the presence of the compound alone, growth, as compared to the un-treated control, was 70% lower for compound 3. For compound 5 growth was lowered 70% (95 ug mL-1) and 60% (47 ug mL-1).

Addition of necrostatin to the incubation with the compound growth for the compound 3 treated cells was 35% and 27% less than the un-treated control. For compound 5 growth in the presence of necrostatin was 43% lower than the control. Necrostatin rescued over 30% of the cells from the negative effect of compound 3. For compound 5, necrostatin rescued 17-27% of the cells. From these results it is evident that bathimodiolamides C(3) and D(5) have an opposite mode of action compared to necrostatin. Consequently, the choice of bathymodiolamides as necrosis inducer for killing cancer cell is verified. Bathymodiolamides can act alone or in combination with other compounds (e.g. with apoptosis inducers) to complete and increase the efficacy on the cancer cell to be treated.

Example 4. HDAC Inhibitor Assay

Figure 14:
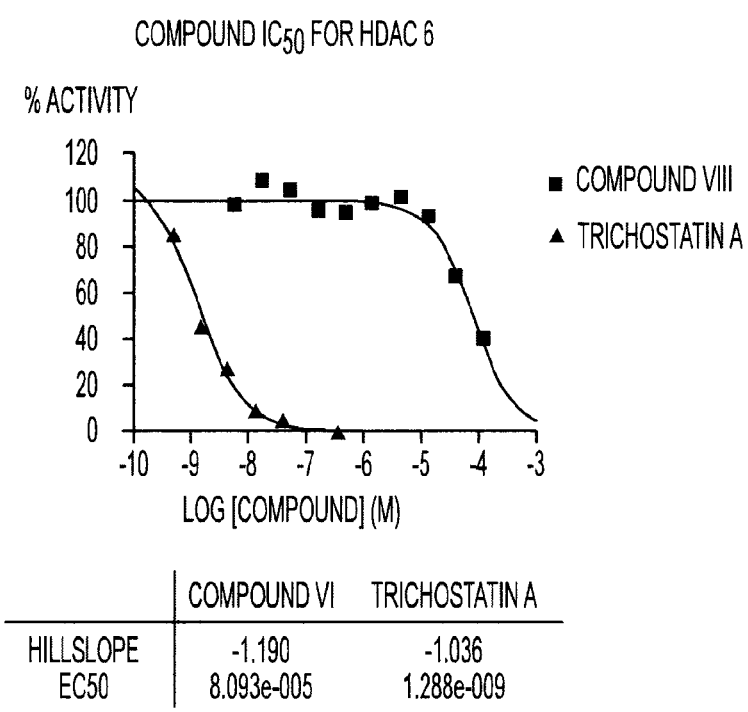
FIG. 14 shows data for the inhibition of HDAC6 by compound VIII ($IC_{50}$ about 80 μM).

Compound VIII was subjected to enzymatic inhibition test against the class I (HDAC1, HDAC2, HDAC3 and HDAC8), the class II A (HDAC4, HDAC5, HDAC7 and HDAC9) and the class II B (HDAC6) enzymes. HDAC inhibitors Trichostatin A (TSA) and TMP269 (TMP) were used as reference compounds. The results showed that compound VIII up to 50 or 100 µM did not significantly inhibit the class I (HDAC1, HDAC2, HDAC3, HDAC8) as well as the class II A (HDAC4, HDAC5, HDAC7, HDAC9), though compound VIII inhibited class II B HDAC6 with $IC_{50}$ around 80 µM (FIG. 14).

Example 5. Other Animal Materials

Given the biodiversity of invertebrate mussels at deep-sea hydrothermal vents, another species of mussel from a deep-sea vent was also extracted and tested. *Bathymodiolus azoricus* was collected using the deep submergence vehicle DSV Alvin from an active hydrothermal vent along the Mid-Atlantic Ridge (Region: North, Location: Lucky Strike (LS), Dive Number: 3119, Date: Jul. 9, 1997, Latitude: 37° 17.394' N, Longitude: 32° 16.672' W, Depth: 1,721 m) and identified by Dr. R. C. Vrijenhoek (formerly of the Department of Marine and Coastal Sciences, Rutgers, The State University of New Jersey) and Dr. C. Vetriani (Department of Biochemistry and Microbiology, Rutgers, The State University of New Jersey). A voucher specimen is available at the Center for Deep-Sea Ecology and Biotechnology, Department of Marine and Coastal Sciences, Rutgers The State University of New Jersey, New Brunswick, N.J. 08901 with collection number AD-MUS-LS-7/09/97.

*Bathymodiolus azoricus* tissue (11.36 g wet mass) was extracted with MeOH to give a polar organic extract (2 g) and 221 mg of this crude extract was fractionated with solid phase extraction cartridge (Normal-phase) to give several fractions. The one that eluted with 50% ethyl acetate and 50% methanol (21 mg) was found to be active when tested with different bioassays.

Example 6

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |

| (iv) Injection 1 (mg/ml) | mg/ml |
|---|---|
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

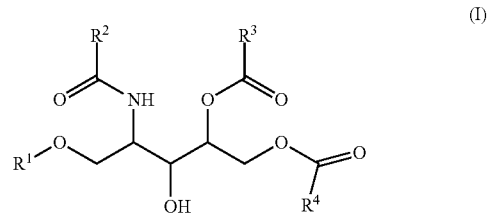

or a pharmaceutically acceptable salt thereof, wherein:
$R^1$ is $R^a$—$(OCH_2CH_2)_n$—;
$R^2$ is $(C_4$-$C_{25})$alkyl or $(C_4$-$C_{25})$alkenyl;
$R^3$ is $(C_4$-$C_{25})$alkyl or $(C_4$-$C_{25})$alkenyl;
$R^4$ is $(C_4$-$C_{25})$alkyl or $(C_4$-$C_{25})$alkenyl;
$R^a$ is $(C_1$-$C_6)$alkyl; and
n is 0, 4, 5, 6, 7, 8, 9, or 10.

2. The compound of claim 1 wherein n is 4, 5, 6, 7, 8, 9, or 10.

3. The compound of claim 1 wherein $R^3$ is $(C_9$-$C_{25})$alkyl.

4. The compound of claim 1 wherein $R^3$ is $(C_{11}$-$C_{20})$alkyl.

5. The compound of claim 1 wherein $R^3$ is $(C_{11}$-$C_{20})$alkenyl.

6. The compound of claim 1 wherein $R^4$ is $(C_9$-$C_{25})$alkenyl.

7. The compound of claim 1 wherein $R^4$ is $(C_{11}$-$C_{20})$alkyl.

8. The compound of claim 1 wherein $R^4$ is $(C_{11}-C_{20})$ alkenyl.

9. The compound of claim 1 wherein $R^a$ is methyl, ethyl, propyl, or isopropyl.

10. The compound of claim 1 wherein $R^a$ is methyl.

11. The compound of claim 1 which is isolated or purified.

12. A method for treating cancer in an animal comprising administering to the animal: 1) an anticancer compound, and 2) a compound of formula (I):

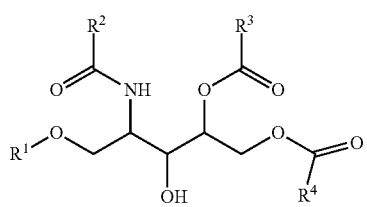
(I)

or a pharmaceutically acceptable salt thereof, wherein:

$R^1$ is $R^a$—$(OCH_2CH_2)_n$—;

$R^2$ is $(C_4-C_{25})$alkyl or $(C_4-C_{25})$alkenyl;

$R^3$ is $(C_4-C_{25})$alkyl or $(C_4-C_{25}$alkenyl;

$R^4$ is $(C_4-C_{25})$alkyl or $(C_4-C_{25})$alkenyl;

$R^a$ is $(C_1-C_6)$alkyl; and n is 0, 4, 5, 6, 7, 8, 9, or 10.

13. The method of claim 12 wherein the anticancer compound induces apoptosis upstream of Bax or Bak.

14. The method of claim 12 wherein the anticancer compound is selected from a group consisting of compounds of formulae III-VIII:

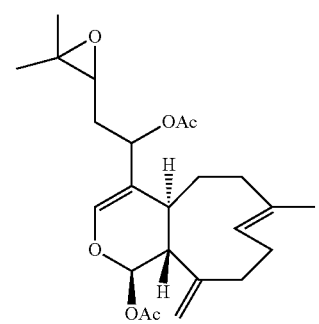
III

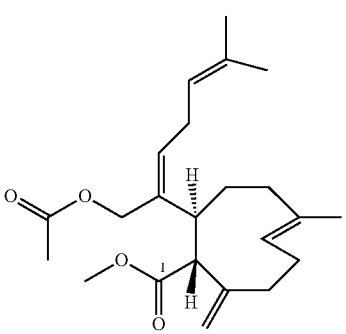
IV

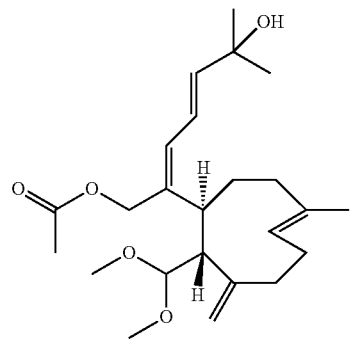
V

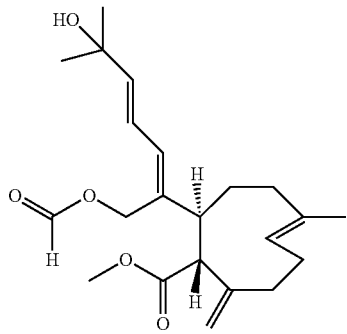
VI

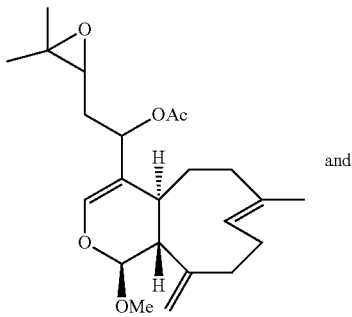
VII and

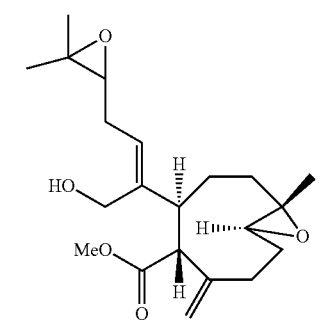
VIII or is a pharmaceutically acceptable salt thereof.

15. A pharmaceutical composition comprising a compound of formula (I) as described in claim 1 or a pharmaceutically acceptable salt thereof, and a pharmaceutically acceptable diluent or carrier.

16. A method for treating cancer in an animal comprising, administering to the animal a compound of formula (I) as described in claim 1 or a pharmaceutically acceptable salt thereof.

17. The pharmaceutical composition of claim 15 further comprising an anticancer compound.

18. The pharmaceutical composition of claim 17 wherein the anticancer compound is an apoptosis inducing compound.

19. The method of claim 12 wherein the anticancer compound is an apoptosis inducing compound.

20. The compound of claim 1 wherein n is 0.

* * * * *

UNITED STATES PATENT AND TRADEMARK OFFICE
CERTIFICATE OF CORRECTION

| | |
|---|---|
| PATENT NO. | : 10,537,545 B2 |
| APPLICATION NO. | : 15/746368 |
| DATED | : January 21, 2020 |
| INVENTOR(S) | : Richard Lutz et al. |

It is certified that error appears in the above-identified patent and that said Letters Patent is hereby corrected as shown below:

In the Specification

Column 1, Lines 14-16, please delete "This invention was made with government support under R37 CA53370 awarded by the National Institutes of Health. The government has certain rights in the invention." and insert -- This invention was made with government support under CA53370 awarded by the National Institutes of Health and grant number 0327373 awarded by the National Science Foundation. The government has certain rights in the invention. -- therefor.

Signed and Sealed this
Tenth Day of January, 2023

*Katherine Kelly Vidal*

Katherine Kelly Vidal
*Director of the United States Patent and Trademark Office*